ID 
US012037361B2

(12) United States Patent
Chow et al.

(10) Patent No.: US 12,037,361 B2
(45) Date of Patent: Jul. 16, 2024

(54) METHODS FOR TREATING MULTIDRUG RESISTANT BREAST CANCER

(71) Applicant: THE HONG KONG POLYTECHNIC UNIVERSITY, Hong Kong (CN)

(72) Inventors: Ming-Cheung Larry Chow, Hong Kong (CN); Kit Ying Choy, Hong Kong (CN); Chin Fung Chan, Hong Kong (CN); Lai King Wong, Hong Kong (CN)

(73) Assignee: THE HONG KONG POLYTECHNIC UNIVERSITY, Hong Kong (CN)

( * ) Notice: Subject to any disclaimer, the term of this patent is extended or adjusted under 35 U.S.C. 154(b) by 0 days.

(21) Appl. No.: 17/823,527

(22) Filed: Aug. 31, 2022

(65) Prior Publication Data

US 2023/0133141 A1 May 4, 2023

Related U.S. Application Data

(60) Provisional application No. 63/260,736, filed on Aug. 31, 2021.

(51) Int. Cl.
| | | |
|---|---|---|
| *A61K 38/00* | (2006.01) | |
| *A61K 9/00* | (2006.01) | |
| *A61K 31/337* | (2006.01) | |
| *A61K 31/475* | (2006.01) | |
| *A61K 31/704* | (2006.01) | |
| *A61K 38/16* | (2006.01) | |
| *C07K 14/00* | (2006.01) | |

(52) U.S. Cl.
CPC ............ *C07K 14/00* (2013.01); *A61K 9/0019* (2013.01); *A61K 31/337* (2013.01); *A61K 31/475* (2013.01); *A61K 31/704* (2013.01); *A61K 38/16* (2013.01); *C07K 2317/76* (2013.01); *C07K 2319/01* (2013.01); *C07K 2319/10* (2013.01)

(58) Field of Classification Search
CPC ............ C07K 2319/10; C07K 2317/76; C07K 2319/01; C07K 14/47; C07K 2319/00; C07K 7/06; C07K 7/08; A61K 9/0019; A61K 31/337; A61K 31/704; A61K 49/0056; A61K 49/00; A61P 35/00
See application file for complete search history.

(56) References Cited

U.S. PATENT DOCUMENTS 9,234,039 B2 1/2016 Corvey et al.

FOREIGN PATENT DOCUMENTS

| WO | 9916465 A1 | 4/1999 | |
|---|---|---|---|
| WO | WO-2004035789 A1 * | 4/2004 | ............ C07K 14/47 |
| WO | 2012158989 A2 | 11/2012 | |
| WO | 2018112226 A1 | 6/2018 | |
| WO | WO2018/112226 A1 * | 6/2018 | ......... C07K 14/4703 |

OTHER PUBLICATIONS

Markman et al. Advanced Drug Delivery Reviews 65 (2013) 1866-1879 (Year: 2013).*
Saber et al. Daru Journal of Pharmaceutical Sciences (2020) 28:295-304 (Year: 2020).*
GenScript, "Complementary Related Biological Terms," GenScript available online at https://www.genscript.com/biology-glossary/search?special=complementary, 18 pages (accessed on Sep. 5, 2023) at p. 6. (Year: 2022).*
Collins et al, PNAS 117 (2020) 4664-4674 (Year: 2020).*
Bouvard et al. Molecular Cell Biology, vol. 4 (2013) 430-442, (Year: 2013).*
De Franceschi et al. PLOS One (2015) 1-16 (Year: 2015).*
Khandia et al. International Journal of Pharmacology (2017) 13 (7): 677-689, (Year: 2017).*
Jong et al. RSC Chem. Bio., (2020) 1 192-203 (Year: 2020).*
Lim et al. Molecular and Cellular Neuroscience (2001) 17:385-397, (Year: 2001).*
Miller et al., Drug Development Research, vol. 35 (1995), pp. 20-32. (Year: 1995).*
Rabideau et al., ACS Central Science, vol. 1, (2015), pp. 423-430. (Year: 2015).*

* cited by examiner

*Primary Examiner* — Thea D' Ambrosio
*Assistant Examiner* — Claudia Espinosa
(74) *Attorney, Agent, or Firm* — S&F/WEHRW

(57) ABSTRACT

The present disclosure provides methods and composition for treating multi-drug resistant cancers, in particular, breast cancers, via administration to a subject the composition including a peptide having a sequence complementary to a highly conserved motif present in substantially all integrins responsible for an integrin-mediated attachment-independent chemoresistance to one or more chemotherapeutic agents. The binding of the sequence of the peptide to the highly conserved motif will enhance accumulation of the chemotherapeutic agents in the tumor-initiating cells and in turn restores the function of the chemotherapeutic agents in the tumor-initiating cells.

14 Claims, 20 Drawing Sheets

Specification includes a Sequence Listing.

| CD44⁺/CD24⁻ population (%) | |
|---|---|
| MCF-7 AC | 2.4 ± 0.9 |
| CSC | 28.6 ± 5.6 |
| MCF-7 MS | 36.7 ± 7.0 |
| A2KO MS | 36.1 ± 7.0 |
| A2KO-A2OX MS | 42.1 ± 6.1 |

FIG. 2E

|  | DOX | PTX | VCR |
|---|---|---|---|
| IC50 / μM | 37.8 ± 3.8 | 9.6 ± 2.9 | 0.5 ± 0.0 |
| IC50 at 3 μM DRI-TAT-SP / μM | 17.6 ± 5.2 | 2.2 ± 1.5 | 0.1 ± 0.0 |
| EC50 of DRI-TAT-SP / μM | 2.3 ± 0.4 | 2.0 ± 0.2 | 1.0 ± 0.4 |

| Route | | i.v. |
|---|---|---|
| Dose | mg/kg | 25 |
| AUC(0-obs) | ng-min/mL | 118,010 |
| $C_{max}$ | ng/mL | 870 |
| $T_{max}$ | min | 5 |
| $t_{1/2\alpha}$ | min | 15.9 |
| $t_{1/2\beta}$ | min | 442 |
| AUC(0-obs)/Dose | | 4,720 |

METHODS FOR TREATING MULTIDRUG RESISTANT BREAST CANCER

CROSS-REFERENCE TO RELATED APPLICATION

This application claims priority from the U.S. provisional patent application Ser. No. 63/260,736 filed Aug. 31, 2021, and the disclosure of which is incorporated herein by reference in its entirety.

REFERENCE TO SEQUENCE LISTING

A Replacement Sequence Listing with a file name "P23496US01_Sequence_Listing.xml" in ST.26 XML format and a file size of 46.7 kb created on Feb. 19, 2024 is incorporated herein by reference.

TECHNICAL FIELD

The present invention relates to methods for treating multi-drug resistant cancers, in particular, to methods for treating multi-drug resistant breast cancer.

BACKGROUND

Breast cancer is the most prevalent cancer among women, impacting 1.5 million women each year and 15% of deaths from all cancers. Although various therapeutic strategies are commonly employed, treated patients can suffer from disease relapse and metastasis due to the presence of cancer stem cells (BCSCs). Breast CSCs (BCSCs) are a subset of tumor population with abilities of self-renewal, quiescence and generating heterogenic lineages of cancer cells. BCSCs possess different intrinsic mechanisms of resistance to current chemotherapeutic drugs, like overexpression of ATP-binding cassette (ABC) transporters family, and activation of different signaling pathways such as Wnt/β-catenin signaling, Notch and Akt survival pathways, being one of the biggest hurdles to effective chemotherapy. Current drugs to reverse chemoresistance such as ABC transporter inhibitors, verapamil, possess many side effects, for example, cardiovascular side effects associated with continuous and high-dose intravenous verapamil therapy.

Integrins are a family of αβ-heterodimeric cell surface receptors that mediate cell adhesion to the surrounding extracellular matrix (ECM), triggering cellular responses such as cell migration and proliferation, contributing to tumor progression, CSC phenotypes and chemoresistance. They are also markers of certain CSCs and able to mediate cell-cell adhesion which helps corresponding stem cells anchor to their niche, in addition to their adhesion to the surrounding substrata. Some studies proposed that integrins contribute to an attachment-dependent chemoresistance through their membrane proximal conserved KXGFFKR (SEQ ID NO: 31) motif, which is critical for receptor functions and activation of 3 integrins. This highly conserved motif in their a integrins can interact with various proteins including calreticulin (CRT), which is a multifunctional protein involved in various cellular activities such as protein folding, phagocytosis, cell proliferation and metastasis. Its abilities to bind ITGA2 and activate ITGB1 prevent cell surface localization of CRT, in turn mediates phagocytosis.

Another function of the highly conserved KXGFFKR (SEQ ID NO: 31) motif is to inhibit ITGB1 by interacting with SHARPIN through its ubiquitin-like (UBL) domain, resulting in inactivation of ITGB1.

Thus, inhibition of integrin activation through interaction with the UBL domain of SHARPIN to compete with CRT for a highly conserved KXGFFKR (SEQ ID NO: 31) motif appears to be a potential mechanism to reserve the chemoresistance in the CSCs arising from interaction between integrin ITGA2 and the highly conserved motif, and the activation of the ITGB1, as the activation of ITGB1 renders cytoplasmic CRT to chemoresistance by degradation of p53 for cell survival (FIG. 9).

SUMMARY

Accordingly, the present disclosure proposes methods and composition for treating multi-drug resistant cancers including breast cancer in a subject in need thereof. The methods include administering to the subject the composition including a peptide, where the peptide includes a cell penetrating sequence and a sequence complementary to a membrane proximal conserved motif present in substantially all integrins in tumor-initiating cells including those associated with integrin-mediated attachment-independent chemoresistance such that the peptide of the composition is capable of reversing the integrin-mediated attachment-independent chemoresistance in the tumor-initiating cells, in order to restore the function of one or more chemotherapeutic agents against the tumor-initiating cells.

In certain embodiments, the peptide of the composition is represented by SEQ ID NO: 4.

In certain embodiments, the cell penetrating sequence is a TAT peptide represented by SEQ ID NO: 1.

In certain embodiments, the membrane proximal conserved motif is a highly conserved KXGFFKR (SEQ ID NO: 31) motif of a integrin.

In certain embodiments, the sequence complementary to the highly conserved KXGFFKR (SEQ ID NO: 31) motif is derived from a ubiquitin-like domain of an endogenous P1-integrin activation inhibitor.

In certain embodiments, the endogenous β1-integrin activation inhibitor is SHARPIN, and the sequence complementary to the highly conserved KXGFFKR (SEQ ID NO: 31) motif is a SHARPIN-derived peptide represented by SEQ ID NO: 2.

In certain embodiments, the TAT peptide and SHARPIN-derived peptide (SP) are synthesized together into a D-retro-inverso (DRI) form for preventing thereof from protease degradation in vivo.

Preferably, the SHARPIN-derived peptide is synthesized based on D-amino acids to make the peptide resistant to enzymatic digestion by endogenous protease when the composition is administered in vivo.

In certain embodiments, the DRI form of the TAT-SP peptide (DRI-TAT-SP) is synthesized by modifying N- and C-termini thereof.

Preferably, the N-terminus of the TAT-SP peptide is acetylated while the C-terminus thereof is amidated to obtain the DRI-TAT-SP peptide.

In certain embodiments, the DRI-TAT-SP peptide is represented by SEQ ID NO: 6.

In certain embodiments, the composition is administered in combination with one or more chemotherapeutic agents to the subject.

In certain embodiments, the one or more chemotherapeutic agents include an anthracycline or a DNA topoisomerase II inhibitor.

In certain embodiments, the one or more chemotherapeutic agents is/are administered as a neoadjuvant therapy prior to the administration of the present composition.

In certain embodiments, the one or more chemotherapeutic agents include doxorubicin (DOX), paclitaxel (PTX) and vincristine (VCR).

In certain embodiments, the composition is administered to the subject via one or more routes including, but not limited to, intravenous and intraperitoneal injections.

In certain embodiments, the subject is human and the multi-drug resistant cancers include human breast cancer.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Other aspects of the present invention are disclosed as illustrated by the embodiments hereinafter.

BRIEF DESCRIPTION OF DRAWINGS

The appended drawings, where like reference numerals refer to identical or functionally similar elements, contain figures of certain embodiments to further illustrate and clarify the above and other aspects, advantages and features of the present invention. It will be appreciated that these drawings depict embodiments of the invention and are not intended to limit its scope. The invention will be described and explained with additional specificity and detail through the use of the accompanying drawings in which:

FIG. 2E shows flow cytometry analysis results of CSC population in MCF-7 AC, CSC and different ITGA2 mutants as in FIG. 2A;

Skilled artisans will appreciate that elements in the figures are illustrated for simplicity and clarity and have not necessarily been depicted to scale.

DETAILED DESCRIPTION OF THE INVENTION

It will be apparent to those skilled in the art that modifications, including additions and/or substitutions, may be made without departing from the scope and spirit of the invention. Specific details may be omitted so as not to obscure the invention; however, the disclosure is written to enable one skilled in the art to practice the teachings herein without undue experimentation.

(1) Role of ITGA2 in Multidrug Resistance in CSCs

Figure 1A:
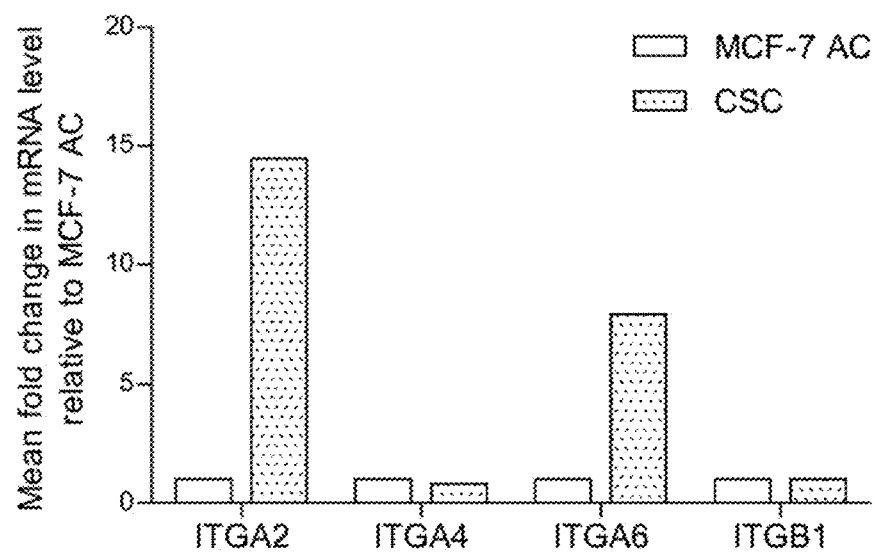
FIG. 1A shows mRNA levels of different integrins in MCF-7 and MCF-7 derived cell lines obtained by using RT2 profiler PCR array; CSC: cancer stem cell.
Figure 1B:
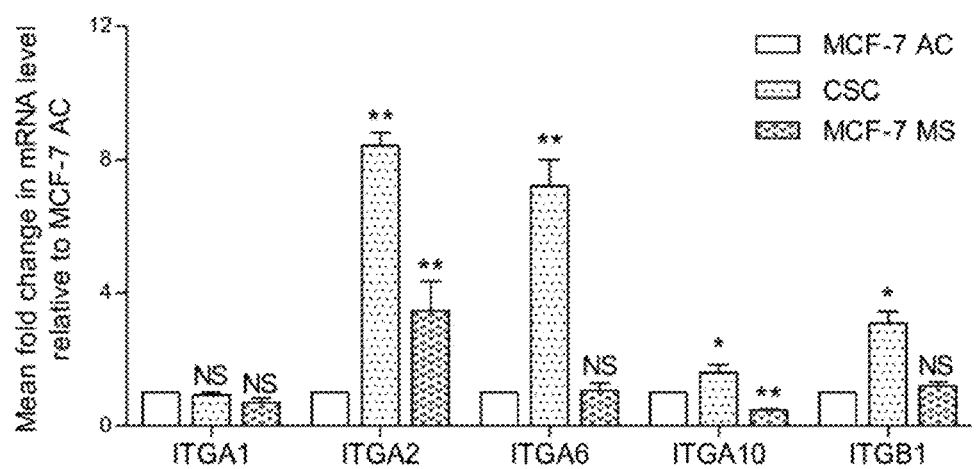
FIG. 1B shows mRNA levels of different integrins in MCF-7 and MCF-7 derived cell lines measured by quantitative real-time PCR (qRT-PCR); * P<0.05 and ** P<0.01 compared to MCF-7 AC; NS: not significant
Figure 1C:
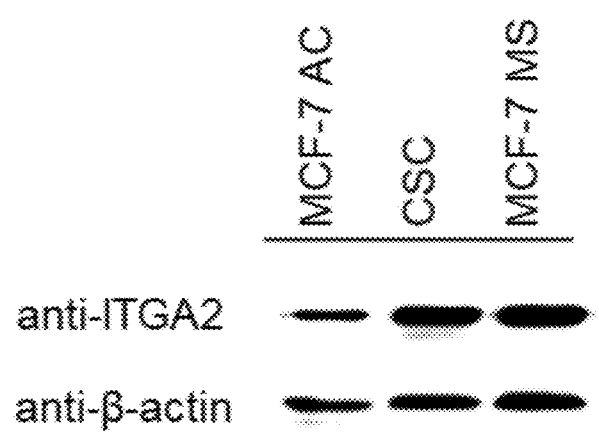
FIG. 1C shows ITGA2 protein levels in MCF-7 and MCF-7 derived cell lines detected by Western Blotting (WB); data shown are representative of independently conducted experiments.

The present disclosure provides methods and related composition for targeting an integrin-mediated attachment-dependent chemoresistance mechanism in cancer stem cells (CSCs) including breast cancer stem cells (BCSCs). ITGA2, a type of integrin, shows the greatest upregulation among 84 genes studied $RT^2$ qPCR primer assay (FIG. 1A) in CSCs sorted from MCF-7 adherent cells (AC), which is confirmed by quantitative PCR (qRT-PCR) and Western Blotting (WB) (FIGS. 1B and 1C).

Figure 2A:
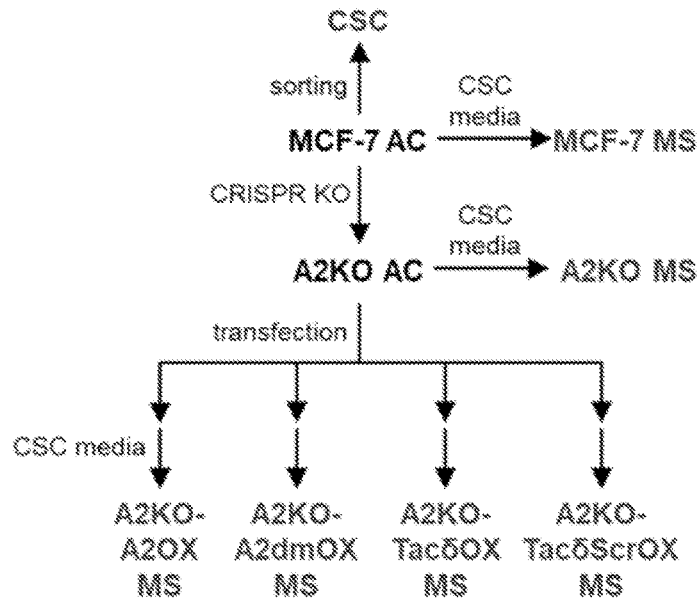
FIG. 2A schematically depicts construction of ITGA2 mutants.
Figure 2B:
FIG. 2B shows ITGA2 constructs used to transfect ITGA mutants as in FIG. 2A; A2 denotes full-length ITGA2; A2dm denotes KLGFFKR (SEQ ID NO: 29) motif-deficient (dm) ITGA2, with the KLGFFKR (SEQ ID NO: 29) motif removed from the cytosolic tail; Tac is an unrelated membrane protein fused to KLGFFKR (SEQ ID NO: 29; Tac6) or scrambled KLRFGFK (SEQ ID NO: 30; Tac6Scr); ECD: extracellular domain; TMD: transmembrane domain.
Figure 2C:
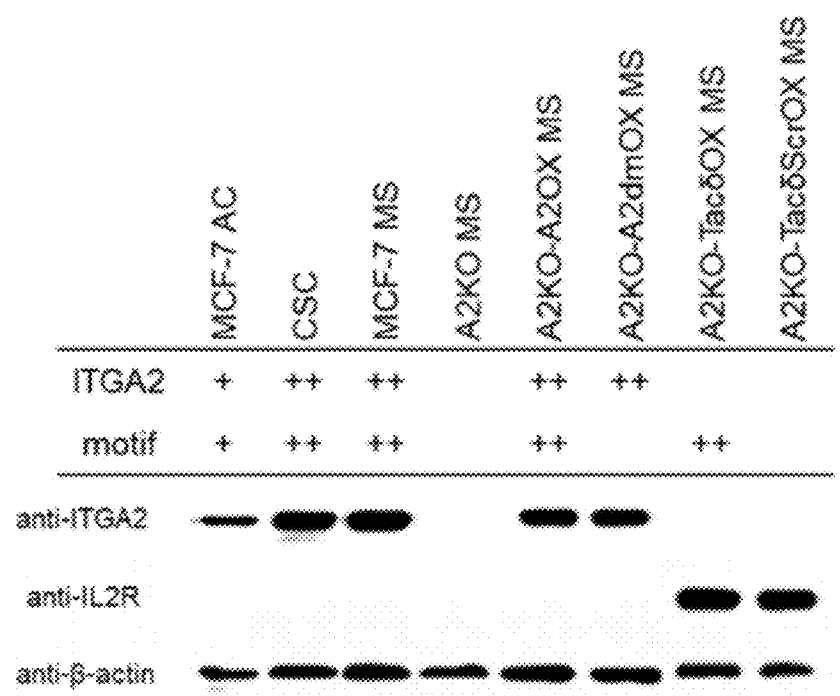
FIG. 2C shows western blot results of ITGA2 and Tac protein levels (using anti-ILR2 antibody) in different ITGA2 mutants as in FIG. 2A.
Figure 2D:
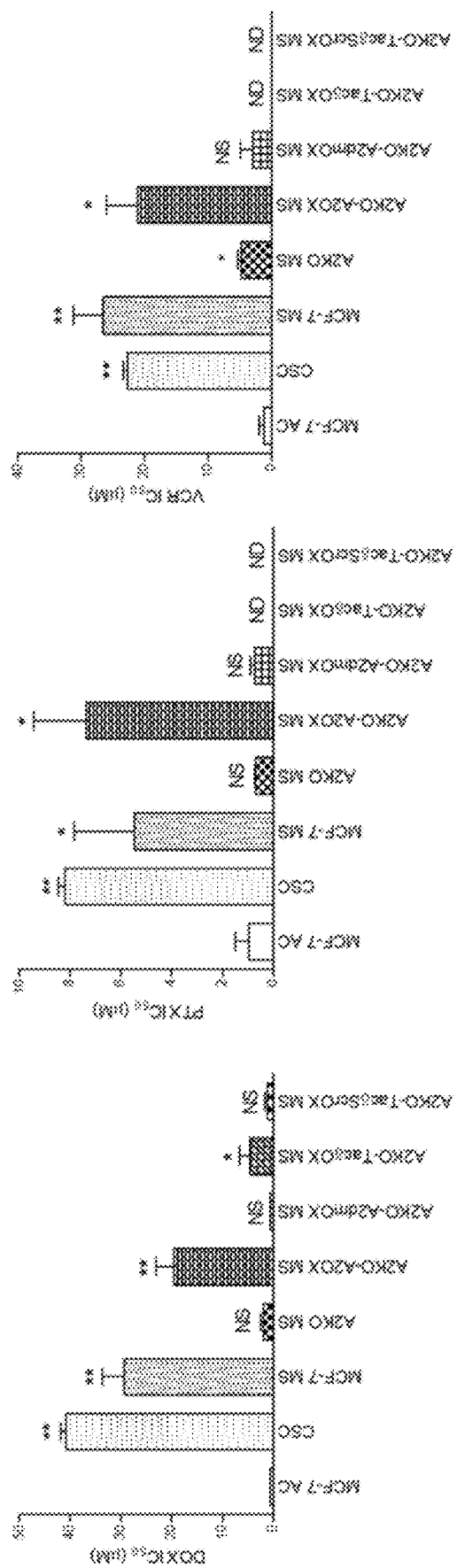
FIG. 2D shows half maximal inhibitory concentration ($IC_{50}$) values of DOX, PTX and VCR in MCF-7 AC, CSC and different ITGA2 mutants as in FIG. 2A.

In order to evaluate the role of ITGA2 in chemoresistance of BCSCs, a knock-out (KO) ITGA2 in vitro model is created in MCF-7 AC, named as A2KO AC, by CRISPR and its mammospheres (A2KO MS) are produced (FIGS. 2A-2C). Compared to its corresponding MCF-7 AC and MS (FIG. 2B), in the absence of ITGA2, A2KO MS remains drug sensitive with a significantly lower drug $IC_{50}$ to DOX, PTX and VCR (FIG. 2C). Reintroduction of full-length ITGA2 to A2KO MS rescues A2KO-A2OX MS from anticancer drugs, confirming the role of ITGA2 in chemoresistance in MS. Such ITGA2-mediated chemoresistance is not due to manipulation of CSC population (FIG. 2E) but other mechanisms.

(2) Role of Conserved Membrane Proximal KXGFFKR (SEQ ID NO: 31) Motif in DOX-Resistant CSCs A highly conserved motif, KXGFFKR (SEQ ID NO: 31), in ITGA2 has been found in all α-integrins. To study the correlation between this conserved membrane proximal motif and drug resistance to DOX, a commonly used chemotherapeutic agent of breast cancer, ITGA2 is overexpressed in A2KO AC by transfection of different ITGA2 plasmids as shown in FIG. 2B into the A2KO AC cells, followed by selection by hygromycin B to derive into several ITGA2 mutants, namely A2KO-ASOX MS, A2KO-ASdmOX MS, A2KO-TacδOX MS, and A2KO-TacδδcrOX MS, where A2KO-ASOX MS denotes the MS derived from A2KO AC with an overexpression of full-length ITGA2 (α-integrin tail: SEQ ID NO: 27); whereas A2KO-ASdmOX MS denotes the MS derived from A2KO AC with an overexpression of KXGFFKR (SEQ ID NO: 31) motif-deficient ITGA2 (by removing KLGFFKR (SEQ ID NO: 29) motif from its cytosolic tail), while A2KO-TacδOX MS denotes the MS derived from ASKO AC with an overexpression of the KXGFFKR (SEQ ID NO: 31) motif alone in Tac6 protein (where Tac is an unrelated membrane protein fused to KLGFFKR motif) and A2KO-TacδδcrOX MS denotes MS derived from ASKO AC with an overexpression of a scrambled KLGFFKR (SEQ ID NO: 30) in Tac6 protein. It is observed that the overexpression of full-length ITGA2 (A2KO-A2OX MS), but not the motif-deficient ITGA2 (A2KO-A2dmOX MS), could successfully rescue the KO clone from DOX. However, overexpression of KXGFFKR (SEQ ID NO: 31) motif alone (A2KO-TacδOX MS) does not fully rescue the KO clone and restore DOX $IC_{50}$, implying that KXGFFKR (SEQ ID NO: 31) motif is required but not sufficient to induce attachment-independent DOX-resistance in MCF-7 CSCs.

Figure 3A:
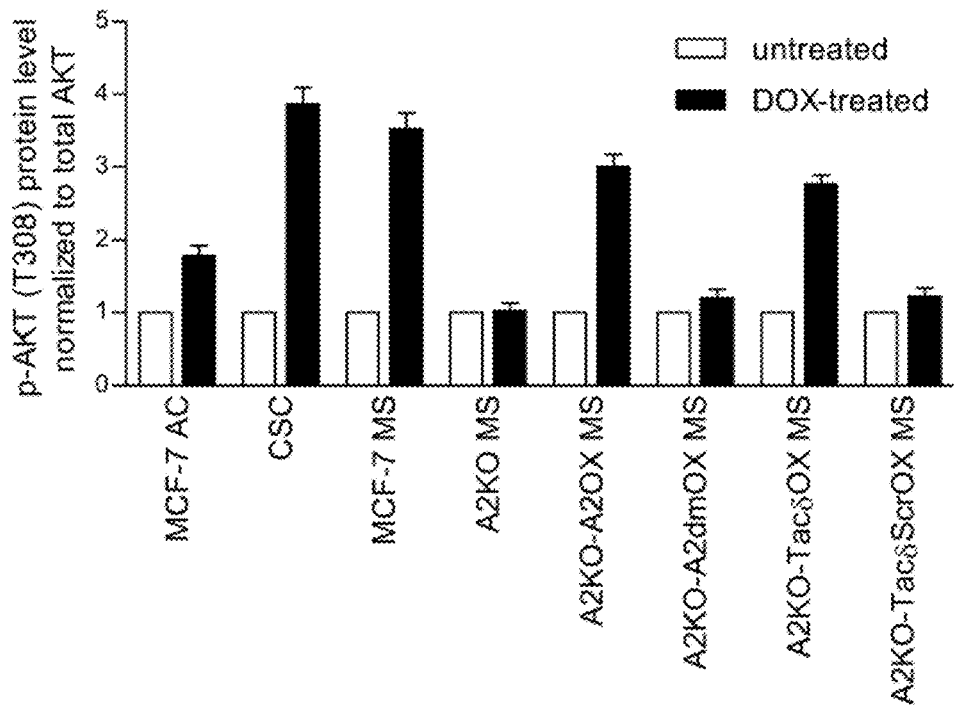
FIG. 3A shows normalized phosphorylated-AKT (p-AKT) protein levels in MCF-7 AC, CSC and different ITGA2 mutants treated with 1 µM DOX for 24 hours at 37° C.

(3) Role of Activation of ITGB1 in DOX Resistance of CSCs Via Stimulation of Akt Pathway by KXGFFKR (SEQ ID NO: 31) Motif ITGA2, through its KXGFFKR (SEQ ID NO: 31) motif, is responsible for activation of ITGB1, which in turn stimulates different downstream pathways including Akt signaling pathway. FIG. 3A shows that ITGA2 mutants with overexpression of full length of ITGA2 (A2KO-A2OX MS) and overexpression of KXGFFKR (SEQ ID NO: 31) motif (A2KO-TacδOX MS) have elevated DOX-induced Akt phosphorylation (elevated T308-phosphorylated Akt level), whereas 5473-phosphorylated Akt level remains unchanged upon DOX incubation, excluding its participation in KXGFFKR (SEQ ID NO: 31) mediated DOX-resistance.

Figure 3B:
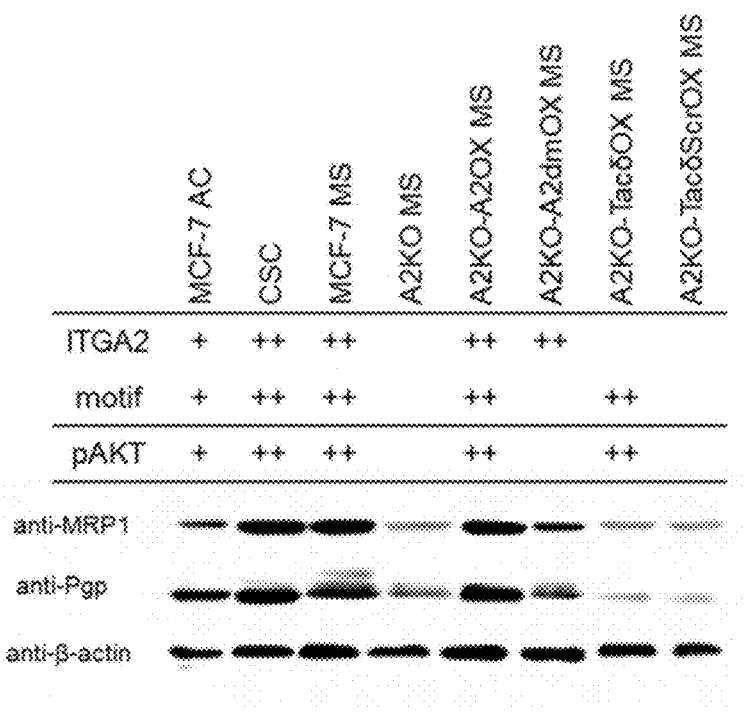
FIG. 3B shows western blot results of MRP1 and P-gp protein expressions in MCF-7 AC, CSC and different mutants with the same treatment as in FIG. 3A.
Figure 3C:
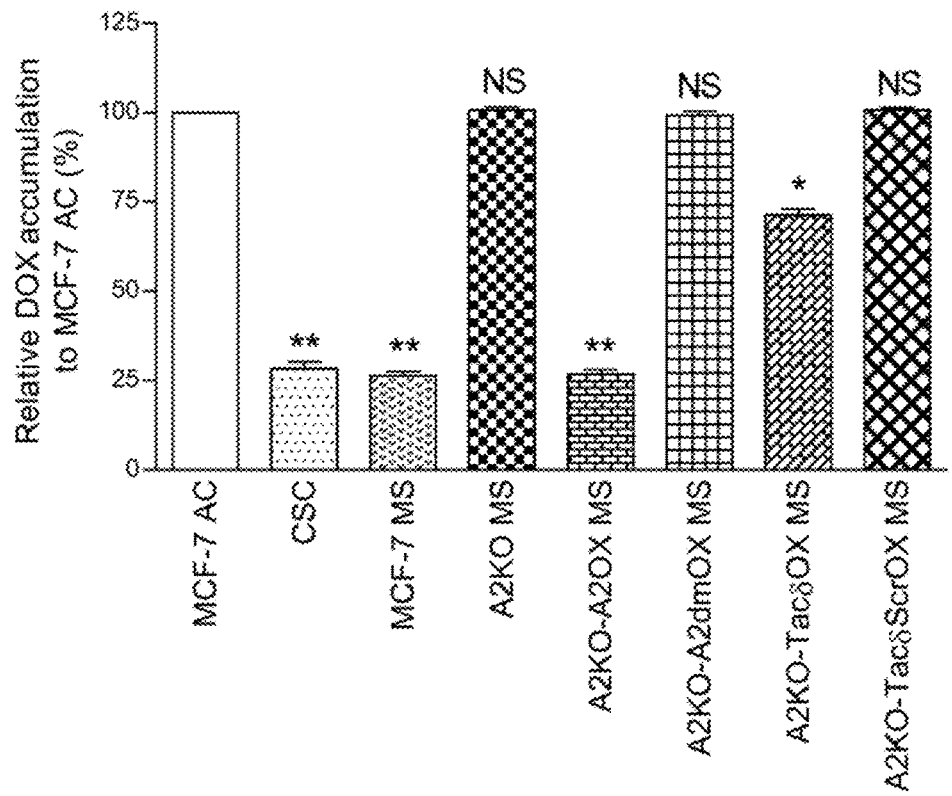
FIG. 3C shows relative DOX accumulation in CSC and different ITGA2 mutants with respect to MCF-7 AC treated with 5 µM DOX for 2 hours at 37° C.; the DOX accumulation is indicated by fluorescence signal from their cell-free supernatants; data shown are representative of at least 3 independently conducted experiments (mean±S.E.M.); * P<0.05 and ** P<0.01 compared to MCF-7 AC; NS: not significant.

Stimulation of Akt pathway leads to upregulation of ABC transporters and enhanced drug efflux activity to mediate drug resistance in CSCs. FIG. 3B shows that overexpression of full-length ITGA2 (A2KO-A2OX MS) upregulates MRP1 and P-gp, but not motif-deficient ITGA2 (A2KO-A2dmOX MS) or KXGFFKR (SEQ ID NO: 31) motif alone (A2KO-TacδOX MS). With upregulation of MRP1 and P-gp, CSC, MCF-7 MS and A2KO-A2OX MS exhibit enhanced DOX efflux, resulting in low DOX accumulation (FIG. 3C). In the absence of KXGFFKR (SEQ ID NO: 31) motif, Akt pathway could not be activated in A2KO-A2dmOX MS for enhanced drug efflux activity and accumulated high level of DOX, even though the MRP1 and P-gp levels are relatively higher when compared to A2KO MS. On the other hand, KXGFFKR (SEQ ID NO: 31) motif alone in A2KO-TacδOX MS is sufficient to activate Akt pathway, allowing it to efflux DOX more efficiently and in turn accumulates relatively less DOX.

Figure 3D:
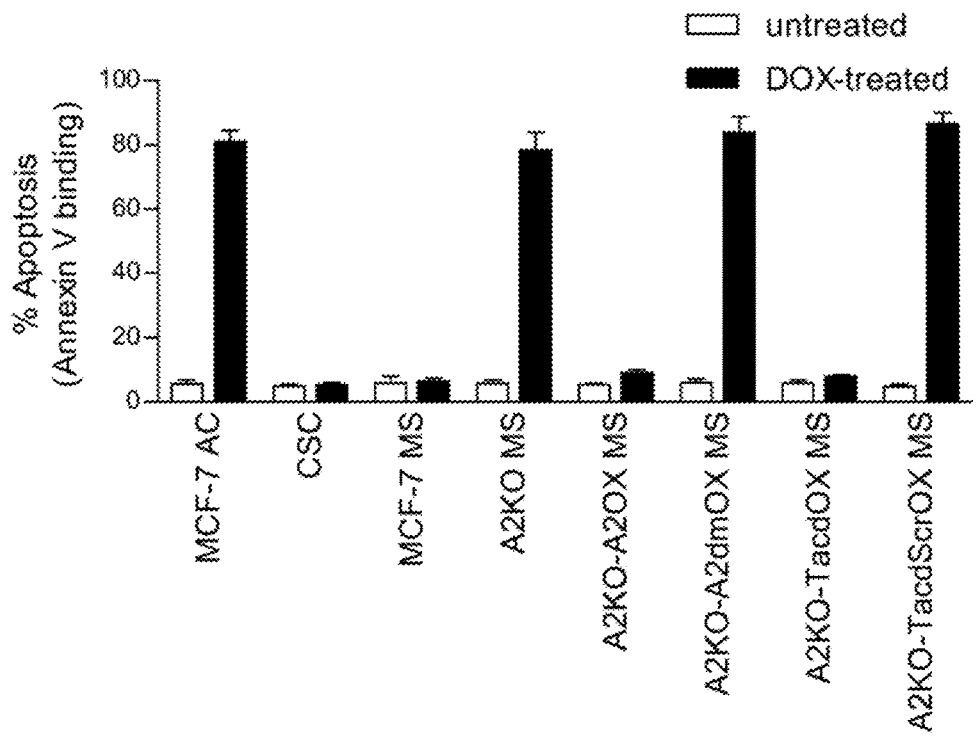
FIG. 3D shows percentages of apoptosis by quantifying annexin V expression level in MCF-7 AC, CSC and different ITGA2 mutants via flow cytometry analysis of annexin V-FITC and propidium iodide positive staining of the cells.

Activation of Akt pathway by ITGA2 is also susceptible to DOX resistance via inhibition of DOX-induced apoptosis. To verify this potential mechanism, an annexin V apoptosis assay is performed on different ITGA2 mutants. Consistent with the results obtained from DOX-induced Akt phosphorylation in FIG. 3C, KXGFFKR (SEQ ID NO: 31) motif of ITGA2 is sufficient to activate Akt pathway to promote cell survival and inhibit DOX-induced apoptosis (FIG. 3D).

Figure 4A:
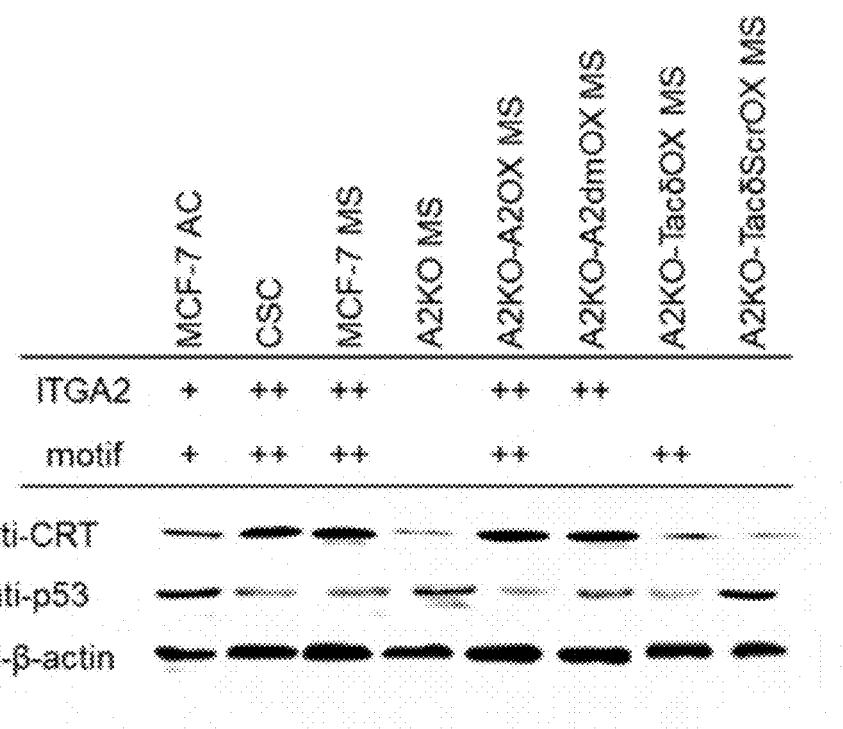
FIG. 4A shows western blot results of CRT and total p53 protein levels in MCF-7 AC, CSC and different ITGA2 mutants with respect to KXGFFKR (SEQ ID NO: 31) motif (motif) interaction with the ITGA2 in the cells.

(4) Role of Interaction Between KXGFFKR (SEQ ID NO: 31) Motif and Calreticulin (CRT) in ITGB1 Activation and DOX Resistance CRT is a multifunctional protein involved in various cellular activities like protein folding, phagocytosis, cell proliferation and metastasis. CRT binds to ITGA2 and helps activate ITGB1, which in turn prevents cell surface localization of CRT and mediates phagocytosis. FIG. 4A shows that the total CRT expression elevates in CSCs and MS with overexpression of full-length ITGA2 but not the KXGFFKR (SEQ ID NO: 31) motif alone, which is consistent with some other studies.

Figure 4B:
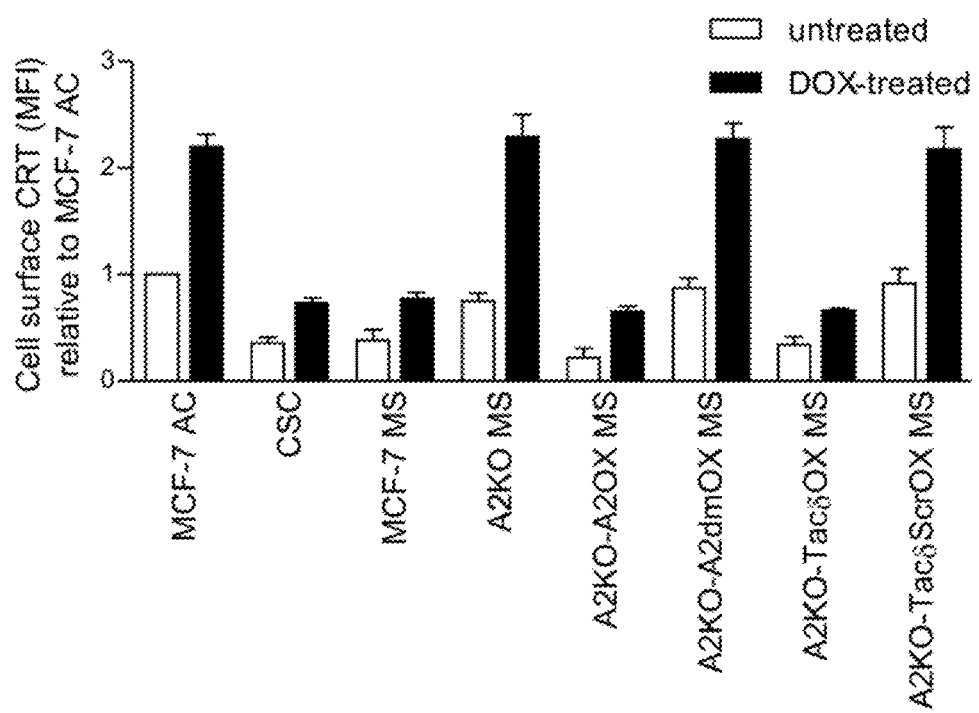
FIG. 4B shows relative cell surface CRT expression in CSC and different ITGA2 mutants with respect to MCF-7 AC with or without DOX treatment in the presence of the motif as in FIG. 4A, which is analyzed by flow cytometry.
Figure 4C:
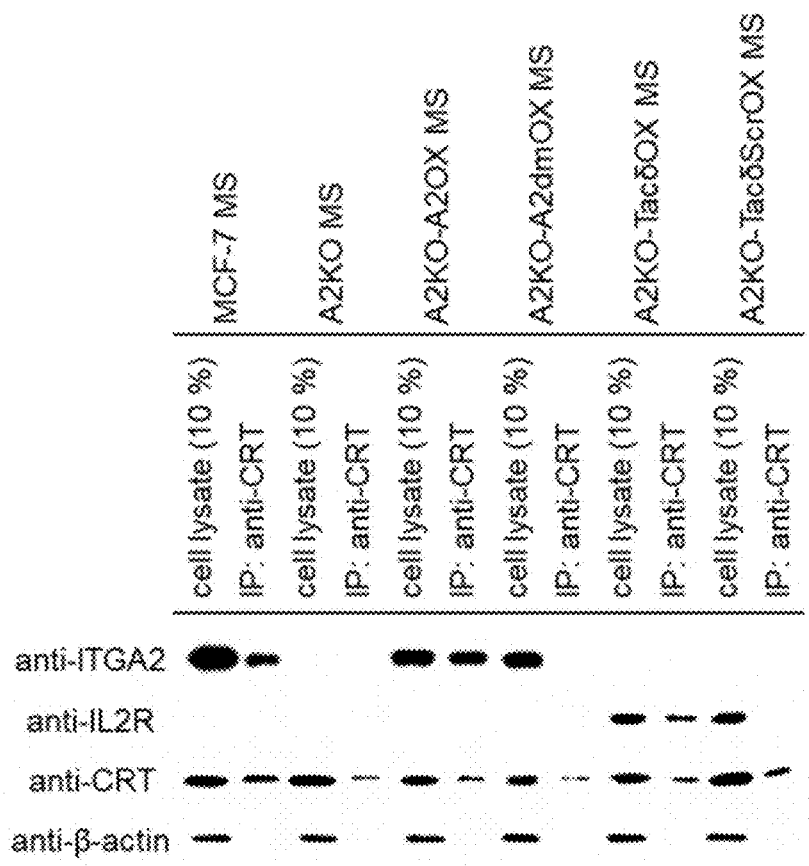
FIG. 4C shows CRT expression level in cell lysate from different ITGA2 mutants by co-immunoprecipitation of different mutants with anti-CRT antibody and analyzed by blotting; data shown are representative of at least 3 independently conducted experiments (mean±S.E.M.)

To assess whether CRT is involved in activation of ITGB1 and ITGA2-mediated DOX-resistance, cell surface CRT localization is measured by indirect immunofluorescence staining with flow cytometry. FIG. 4B shows that the KXGFFKR (SEQ ID NO: 31) motif at ITGA2 (CSC, MS and A2KO-A2OX MS) or Tacδ protein (A2KO-TacδOX MS) interacts with CRT and prevents its surface localization, regardless of total CRT expression level as shown in FIG. 4A. FIG. 4C shows that CRT is co-immunoprecipitated (co-IP) with full-length ITGA2 but not the motif-deficient ITGA2. Similarly, intact KXGFFKR (SEQ ID NO: 31) motif allows co-immunoprecipitation of Tacδ protein with CRT, but not the scrambled motif, confirming the physical interaction between KXGFFKR (SEQ ID NO: 31) motif and CRT. These results indicate that CRT interacts with KXGFFKR (SEQ ID NO: 31) motif of full-length ITGA2, helps activate ITGB1 to simulate the downstream Akt pathway as evident by FIG. 3A, and prevents subsequent cell surface localization (FIG. 4B).

Cytoplasmic CRT is known to promote cell survival and inhibit metastasis through activation of MAPK pathway and degradation of p53. FIGS. 4A and 4B show respectively reduced p53 level and reduced cell surface CRT localization in MCF-7 derived cell lines overexpressed with intact KXGFFKR (SEQ ID NO: 31) motif, suggesting that ITGA2 mediates DOX-resistance by interacting with CRT using its KXGFFKR (SEQ ID NO: 31) motif for activation of ITGB1, which in turn (1) stimulates subsequent Akt pathway for reduced DOX-induced apoptosis and enhanced DOX-efflux, and (2) prevents cell surface localization of CRT by capturing them in cytoplasm for cell survival.

Figures 5A, 5B:
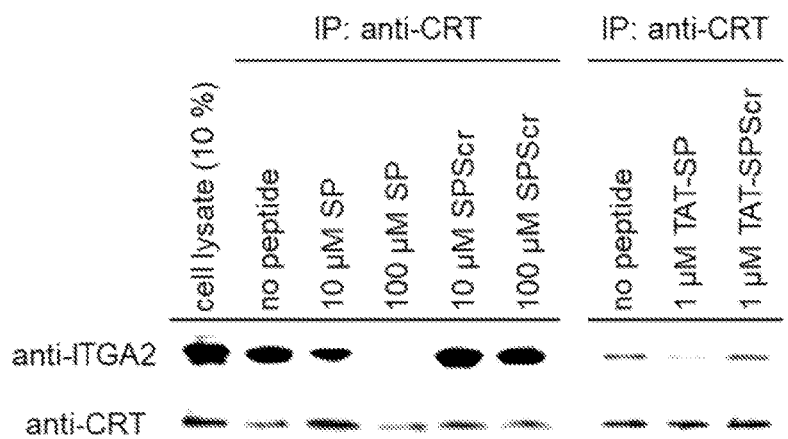
FIG. 5A shows an alignment of different SHARPIN-derived peptides according to certain embodiments of the present invention.
FIG. 5B shows blotting results of from CSC lysate immunoprecipitated with anti-CRT antibody in the presence of different concentrations of SP and SPScr peptides, respectively (left panel) and from CSC lysate immunoprecipitated with anti-CRT in the presence of 1 µM TAT-SP and TAT-SPScr peptides, respectively (right panel) for 24 hours.
Figure 5C:
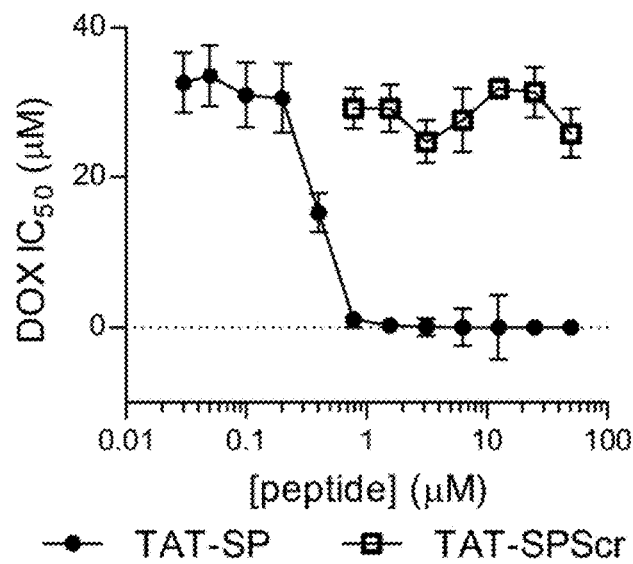
FIG. 5C shows half maximal effective concentration ($EC_{50}$) values of DOX in CSCs treated with TAT-SP and TAT-SPScr peptides, respectively.
Figure 5D:
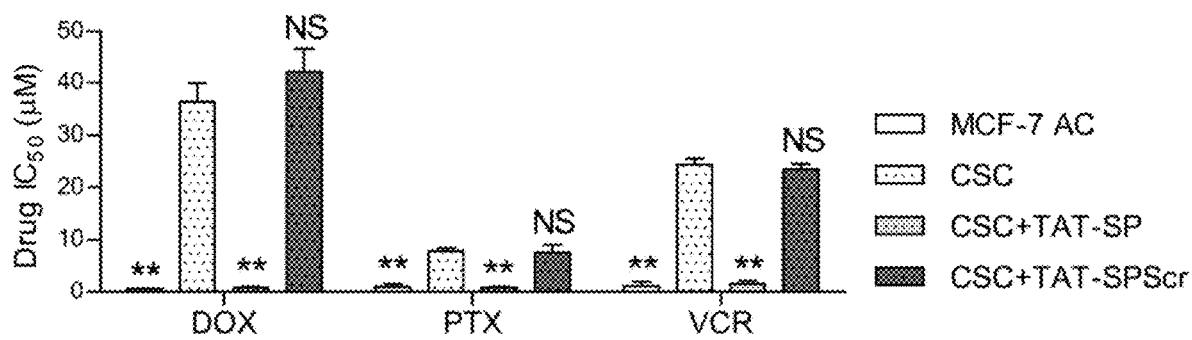
FIG. 5D shows half maximal inhibitory concentration ($IC_{50}$) values of DOX, PTX and VCR in CSCs treated with TAT-SP and TAT-SPScr peptides, respectively; data shown are representative of at least 3 independently conducted experiments (mean±S.E.M.); * P<0.05 and ** P<0.01 compared to CSC; NS: not significant. IP: immunoprecipitation.

(5) Use of SHARPIN-Derived TAT-Peptide to Reverse Chemoresistance in DOX-Resistant CSCs by Competition with CRT for KXGFFKR (SEQ ID NO: 31) Motif SHARPIN, an inhibitor of ITGB1, can interact with the highly conserved KXGFFKR (SEQ ID NO: 31) motif of α-integrin. More specifically, a ubiquitin-like (UBL) domain of the SHARPIN interacts with that motif to inactivate ITGB1. In this regard, a SHARPIN-derived (SP) peptide (SEQ ID NO: 2) derived from the UBL domain of the SHARPIN (residues 259-281) is synthesized (FIG. 5A). FIG. 5B demonstrates that both SP peptide and TAT-SP peptide (SEQ ID NO: 4), but not SPScr (SEQ ID NO: 3) or TAT-SPScr (SEQ ID NO: 5), compete with CRT for the KXGFFKR (SEQ ID NO: 31) motif and inhibit the immunoprecipitation of ITGA2, respectively, confirming the interaction between the UBL domain of SHARPIN and KXGFFKR (SEQ ID NO: 31) motif of ITGA2. TAT-SP peptide, but not TAT-SPScr, is able to modulate CSC chemoresistance with respect to DOX, PTX and VCR (FIG. 5D) in the presence of DOX with $EC_{50}$ of 0.4 μM (FIG. 5C).

Figure 6A:
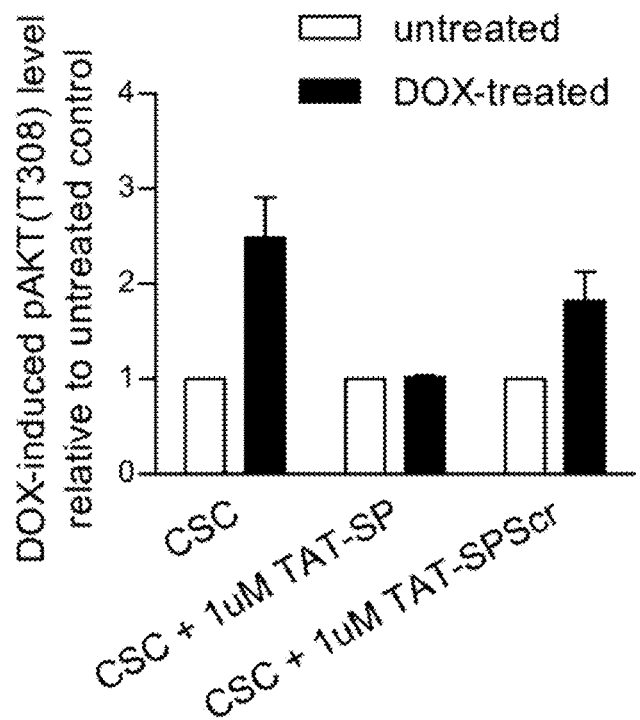
FIG. 6A shows quantification of p-Akt (T308) protein expression in CSCs treated with or without 1 µM TAT-SP or TAT-SPScr peptide for 24 hours.
Figure 6B:
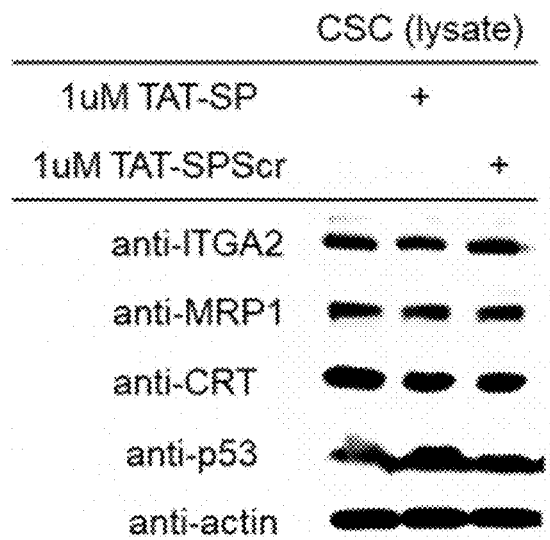
FIG. 6B shows blotting results of ITGA2, MRP1, CRT and p53 protein levels in CSC lysate from cells treated with 1 µM TAT-SP and TAT-SPScr peptides, respectively, for 24 hours.
Figure 6C:
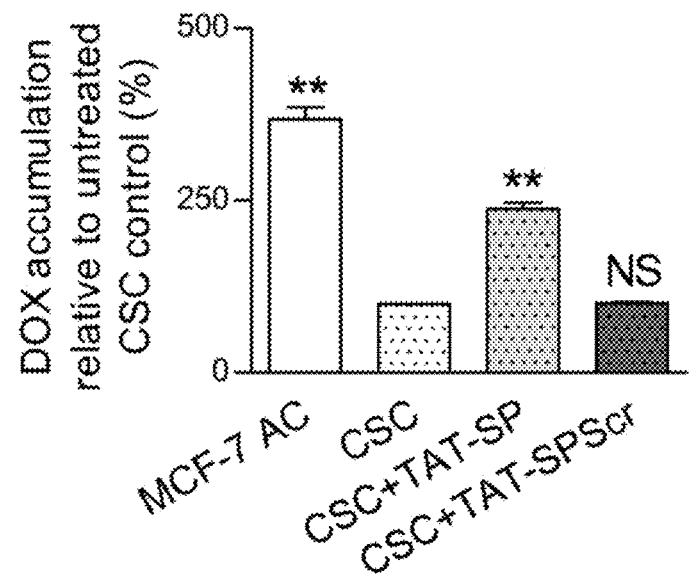
FIG. 6C shows relative percentage of DOX accumulation in different CSC groups treated with 5 µM DOX in the presence of 1 µM TAT-SP and TAT-SPScr peptides, respectively, for 24 hours, with respect to the untreated CSC control group and MCF-7 AC; data shown are representative of at least 3 independently conducted experiments (mean±S.E.M.). * P<0.05 and ** P<0.01 compared to CSC; NS: not significant.
Figure 6D:
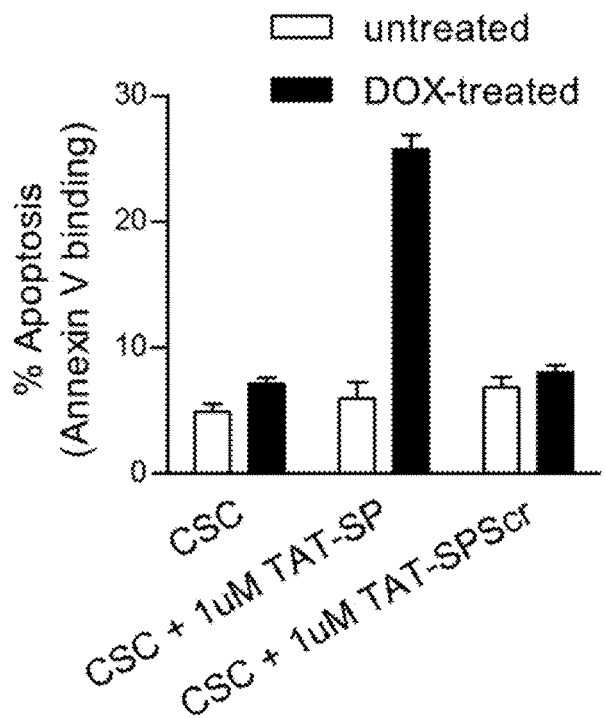
FIG. 6D shows percentages of apoptosis by quantifying annexin V expression level in untreated CSC control group and CSC groups treated with 1 µM TAT-SP and TAT-SPScr peptides, respectively, via flow cytometry analysis of annexin V-FITC and propidium iodide positive staining of the cells.

FIG. 6A shows that incubation of CSCs with TAT-SP peptide inhibits the activation of Akt pathway by ITGA2, but neither the protein expression of ITGA2 nor MRP1 (FIG. 6B). In the absence of enhanced drug efflux by Akt pathway, MRP1 could not efficiently conduct DOX efflux, resulting in high level of DOX accumulation (FIG. 6C). At the same time, inhibition of Akt pathway by TAT-SP leaves CSCs unprotected from DOX-induced apoptosis (FIG. 6D), reversing DOX-resistance in CSC.

(6) Pharmacokinetics of DRI-TAT-SP

Figures 7A, 7B:
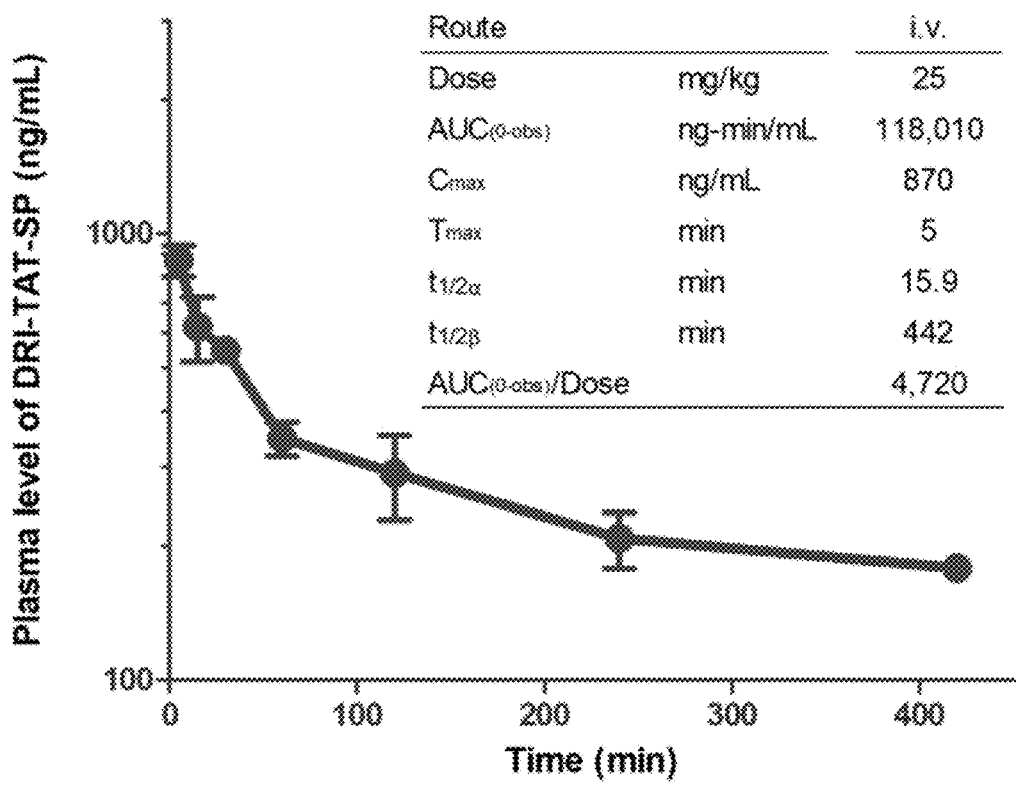
FIG. 7A shows half maximal inhibitory concentration ($IC_{50}$) values of DOX, PTX and VCR in MCF-7 CSC at various concentration in the absence or presence of 3 µM of D-retro-inverso form of TAT-SP peptide (DRI-TAT-SP) according to certain embodiments, and half maximal effective concentration ($EC_{50}$) of the DRI-TAT-SP in reversing chemoresistance to DOX, PTX and VCR in MCF-7 CSC, respectively.
FIG. 7B shows plasma concentration of the DRI-TAT-SP administered at 25 mg/kg by intravenous (i.v.) injection to a breast cancer animal model; $AUC_{(0-obs)}$: Area under the plasma concentration-time curve from time 0 up to 7 hours; $C_{max}$: maximum plasma concentration; $T_{max}$: time to maximum plasma concentration; $AUC_{(0-obs)}$/DOSE: dose normalized area under the plasma concentration-time curve from time 0 up to 7 hours; the values are presented as mean±SD. n=1-3.

To achieve a better peptide stability, a D-retro inverso (DRI) peptide of TAT-SP, namely DRI-TAT-SP, is synthesized, which is shown to be effective in reversing chemoresistance in BCSCs in the presence of DOX with $EC_{50}$ of 2.3±0.4 μM (FIG. 7A).

Six- to eight-week-old female Balb/c mice are administered with DRI-TAT-SP intravenously (i.v.) at 25 mg/kg, and the peptide plasma concentration is monitored from 0 to 7 hrs. FIG. 7B shows that DRI-TAT-SP reaches a $C_{max}$ at 870 ng/mL 5 min post administration, and exhibits a rapid distribution rate at $t_{1/2\alpha}$ of 15.9 min. The elimination phase is observed 60 min post i.v. administration at $t_{1/2\beta}$ of 442 mins.

(7) In Vivo Toxicity of DRI-TAT-SP

Figure 7C:
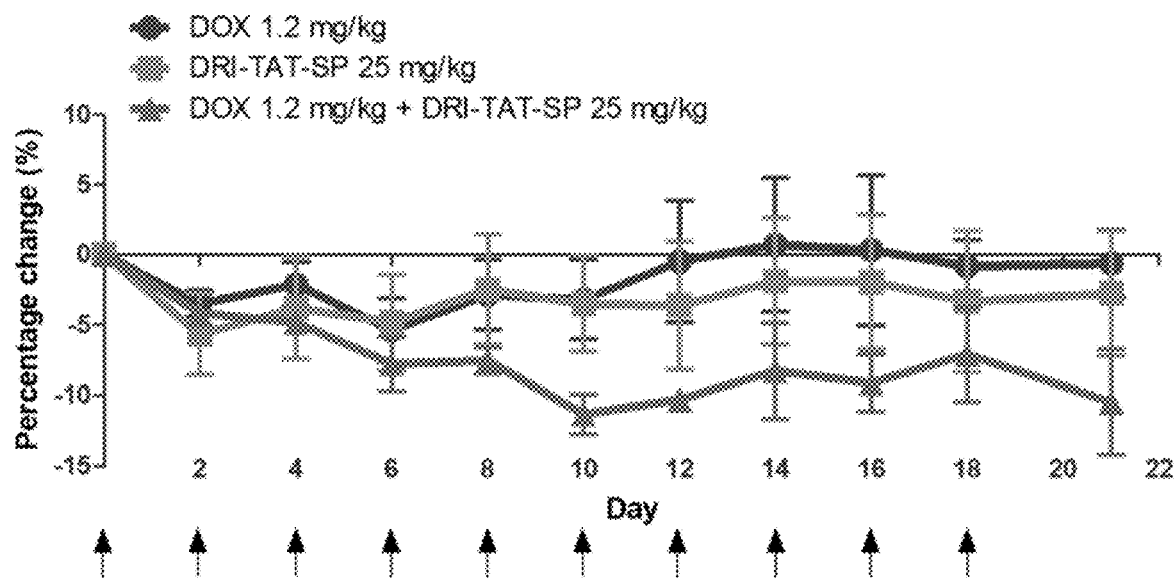
FIG. 7C shows body weight change in the animal model administered with the DRI-TAT-SP as in FIG. 7B, 1.2 mg/kg DOX alone, or both once every two days for 10 injections.
Figure 7D:
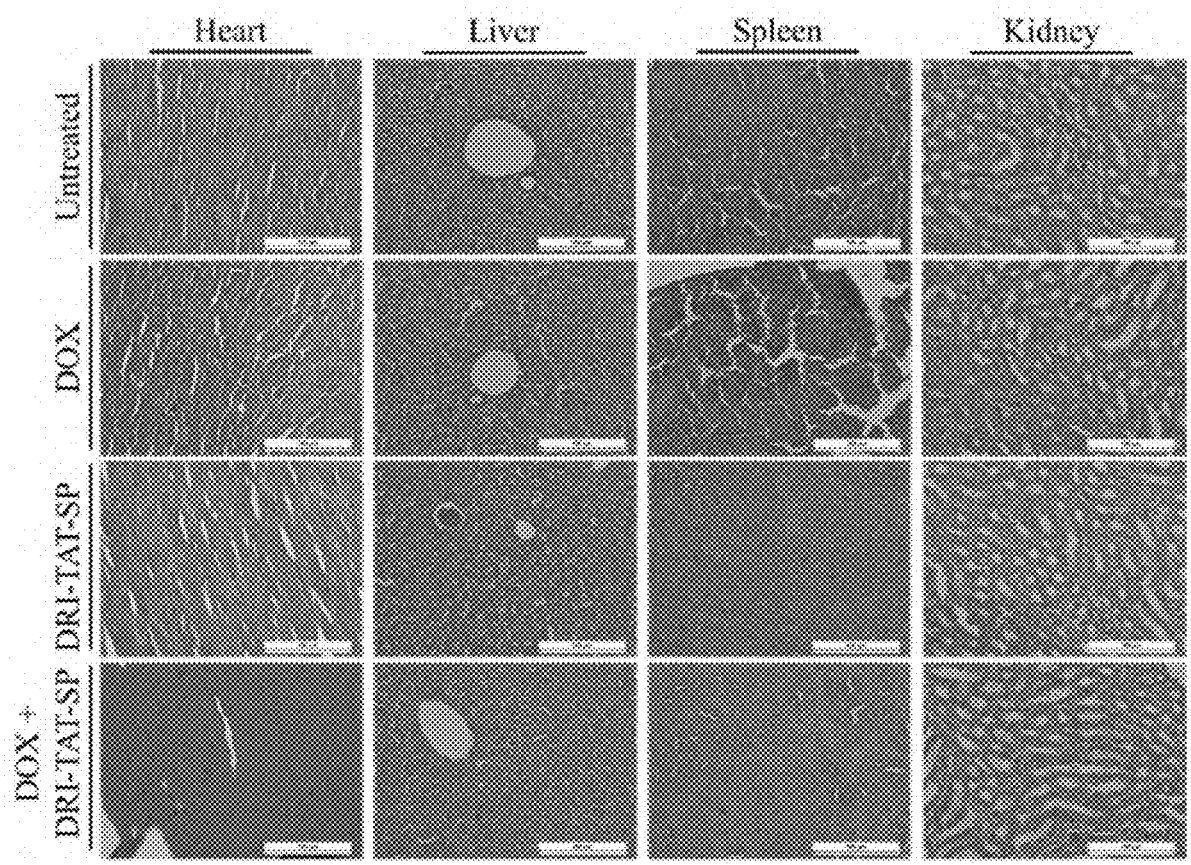
FIG. 7D shows histological examination results of different organs from the animal model after being administered with the DRI-TAT-SP, DOX, or both once every 2 days for 10 injections as in FIG. 7C; the values are presented as mean±SD. n=3-4.

Healthy Balb/c mice are administered intravenously with: (1) DOX 1.2 mg/kg, (2) DRI-TAT-SP 25 mg/kg or (3) DOX 1.2 mg/kg plus DRI-TAT-SP 25 mg/kg once every two days for a total of 10 injections. DRI-TAT-SP alone causes a small drop in body weight by 2.7±4.4% after 10 injections. However, when combined with DOX, the mice suffer from a more significant body weight loss by 10.5±3.7%, given that DOX alone does not cause significant body weight loss (+0.6±2.4%) (FIG. 7C). The organs including heart, liver, spleen, lung, kidneys, and brain are collected after sacrifice, which do not show significance difference in wet weight between the three groups.

(8) DRI-TAT-SP Combined with DOX Significantly Inhibits Tumor Growth in MCF7 Breast Cancer Xenograft The MCF7 human breast cancer xenograft model is established in female Balb/c nude mice supplemented with 17β-estradiol to support the tumor growth. The MCF7 tumor could reach 3.3-fold increase in volume (325±84 mm$^3$) in 20 days with a tumor doubling time of 11.8 days if only PBS was given. DRI-TAT-SP 25 mg/kg alone showed 10.1% tumor inhibition (325±135 mm$^3$) with no statistical significances (P>0.1) while DOX 1.2 mg/kg alone could only inhibit the tumor growth by 21.5% (270±73 mm$^3$, P<0.1)

Figure 8A:
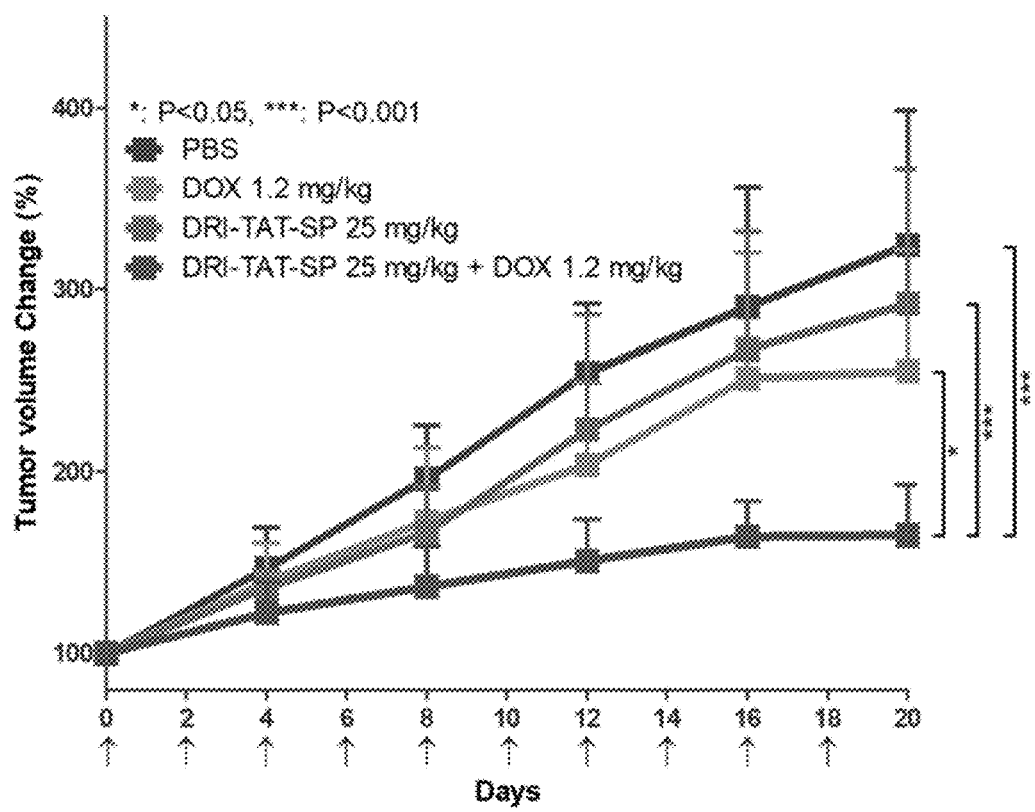
FIG. 8A shows tumor volume change (%) in different treatment groups of animal model with (1) PBS, (2) 1.2 mg/kg DOX, (3) 25 mg/kg DRI-TAT-SP and (4) 1.2 mg/kg DOX+25 mg/kg DRI-TAT-SP, at a frequency of once every 2 days for 10 times via i.v. injection (upper panel); tumor volume is measured using digital caliper once every 4 days (lower panel), where an estimated tumor volume ($mm^3$) is calculated as ½×length×$width^2$ in mm and normalized to the tumor volume on the first day of treatment; the values are presented as mean±SD; n=8-10.
Figure 8A:
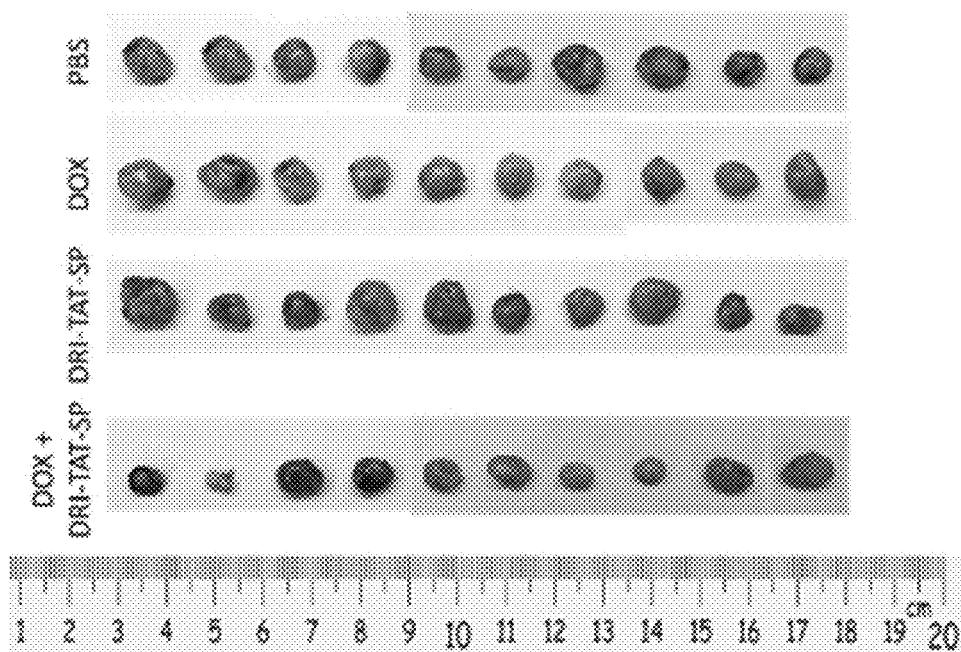
Figure 8B:
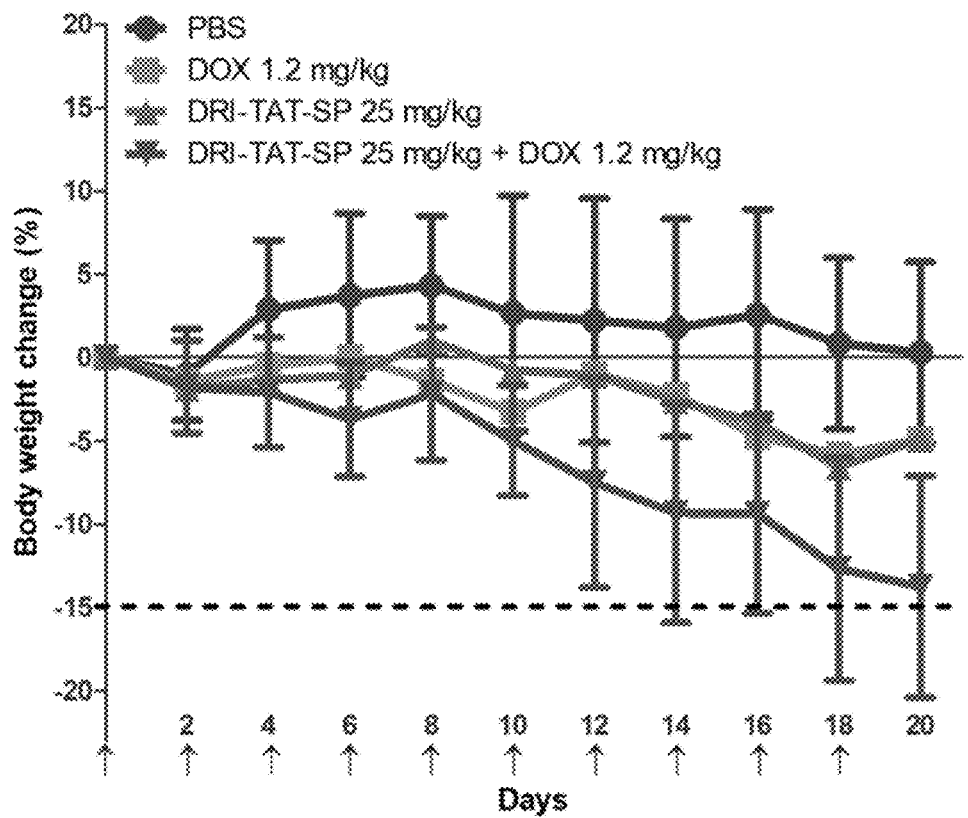
FIG. 8B shows body weight change in different treatment groups of the animal model treated and sampled according to administration scheme as in FIG. 8A.
Figure 8C:
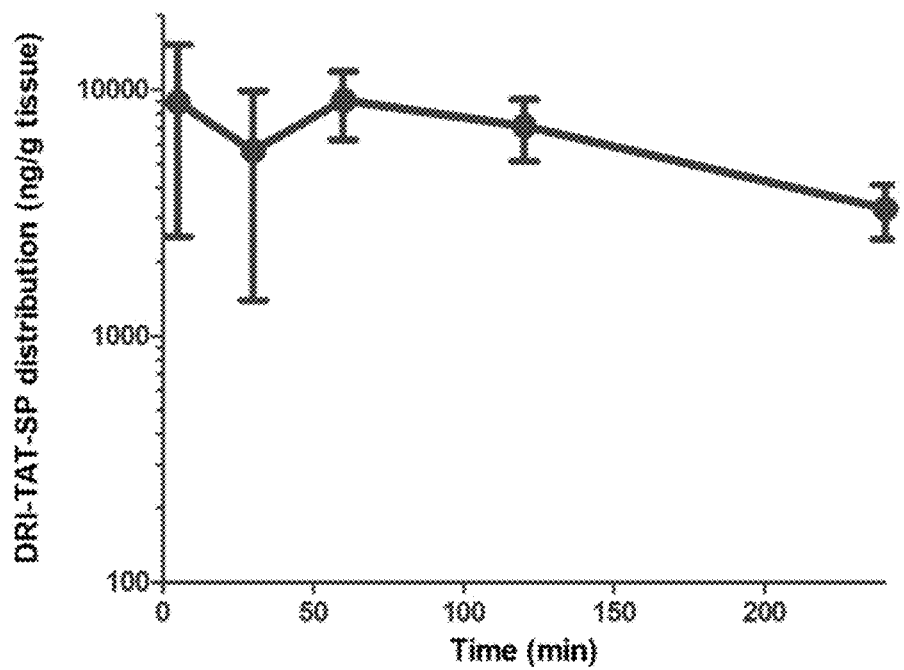
FIG. 8C shows an in vivo DRI-TAT-SP accumulation in tumors over time after i.v. injection; the values are presented as mean±SD; n=2-4.

(FIG. 8A & Table 1). The $T_d$ for DRI-TAT-SP and DOX alone groups are nearly identical (DOX alone: 14.8 days; DRI-TAT-SP alone: 12.9 days). However, the DOX/DRI-TAT-SP combination could significantly reduce the tumor volume by 49.2% (202±63 mm³, P<0.001), delaying the tumor growth at $T_d$ of 27.7 days which is 2.3-fold slower compared to the PBS control group (Table 1). The rapid distribution of DRI-TAT-SP to tumor at around 10,000 ng/g tumor tissues 5 minutes administration further supported its effectiveness in DOX sensitization to kill the breast cancer cells in vivo (FIG. 8C). The DOX/DRI-TAT-SP combination causes 13.7±6.6% body weight drop throughout the study (FIG. 8B). No treatment-induced deaths are observed in all the four groups. However, because of estrogen support, 7 out of 36 mice died of urolithiasis, showing symptoms of depression and dehydration (Table 1).

TABLE 1

Summary of in vivo efficacy and toxicity of doxorubicin combined with DRI-TAT-SP in treating MCF7 breast cancer.

| Treatment group | Animals (n) | Tumor doubling time (Days) | Tumor inhibition (%) | No. of toxicity death |
|---|---|---|---|---|
| PBS | 10 | 11.8 | 0 | 0/8 |
| Doxorubicin (1.2 mg/kg) | 8 | 14.8 | 21.5 | 0/8 |
| DRI-TAT-SP (25 mg/kg) | 8 | 12.9 | 10.1 | 0/6 |
| Doxorubicin (1.2 mg/kg) + DRI-TAT-SP (25 mg/kg) | 10 | 27.7 | 49.2 | 0/7 |

Data obtained are analyzed to evaluate treatment outcomes. Tumor doubling time is calculated using tumor volumes obtained from the end of experiment versus the tumor volumes on the first day of treatment. Tumor inhibition (%) is calculated using the tumor volumes obtained from the end of experiment. Corresponding equations of determining tumor inhibition (T/C) and tumor doubling time (Td) are provided as follows:

$$\text{Tumor inhibition}(T/C) = \left[1 - \frac{\% \text{ Tumor volume(Treatment group)}}{\% \text{ Tumor volume}(PBS \text{ group})}\right] \times 100\%$$

$$\text{Tumor doubling time}(Td) = (t_2 - t_1)\frac{\log(2)}{\log(\% \text{ tumor volume } 2) - \log \%(\text{tumor volume } 1)}$$

$t_2 t_1$% tumor volume$_2 t_2$% tumor volume$_1 t_1$ where, =Final day; =Initial day;

$t_2 t_1$% tumor volume$_2 t_2$% tumor volume$_1 t_1$=Percentage change in tumor volume at;

$t_2 t_1$% tumor volume$_2 t_2$% tumor volume$_1 t_1$=Percentage change in tumor volume at In summary, the present disclosure proposes that an attachment-independent, ITGA2 KXGFFKR (SEQ ID NO: 31) motif-mediated chemoresistance mechanism in BCSCs is a potential target to be reversed. Integrin ITGA2 coupled with ITGB1 to serve as a high affinity receptor for collagen type I and its significant upregulation in CSC and MCF-7 MS are crucial to chemoresistance in CSC and MS derived from MCF-7 AC. Silencing ITGA2 significantly reduces anticancer drug $IC_{50}$ in A2KO MS, confirming the role of ITGA2 in chemoresistance. The pronounced effect of ITGA2 is mostly due to the downregulation of other integrins after ITGA2 KO. Reintroduction of full-length ITGA2, but not the motif-deficient ITGA2 or KXGFFKR (SEQ ID NO: 31) motif alone, successfully rescues corresponding mutants, suggesting that KXGFFKR (SEQ ID NO: 31) motif is required but not sufficient to induce attachment-independent chemoresistance. Upon binding to CRT at its KXGFFKR (SEQ ID NO: 31) motif, ITGA2 induces chemoresistance by activation of ITGB1, stimulating subsequent Akt pathway for (1) upregulation of MRP1/P-gp and promotion of their drug efflux activities for enhanced drug efflux; and (2) inhibition of anticancer drug-induced apoptosis. Activated ITGB1 (3) prevents cell surface localization of CRT, confining them at the cytoplasm to promote cell survival. The proposed SHARPIN-derived peptides, TAT-SP and DRI-TAT-SP, compete with CRT for KXGFFKR (SEQ ID NO: 31) motif via their UBL domain of SIRAPIN to disrupt ITGA2/CRT interaction as well as ITGB1 inactivation.

The proposed SHARPIN-derived peptides, TAT-SP and DRI-TAT-SP, reverse effectively the multidrug resistance in MCF-7 breast CSCs at $DOX-EC_{50}$ of 0.4±0.1 μM and 2.3±0.4 μM, respectively. When combined with DOX at 1.2 mg/kg in vivo, DRI-TAT-SP could suppress the tumor progression in MCF-7 xenograft model by 49.2% after 10 injections in 20 days, showing its potential to treat breast cancers. Although i.v. administration of DRI-TAT-SP at 25 mg/kg does not give a prolonged residence in systemic circulation, a rapid peptide distribution to tumor at around 10,000 ng/g tissues supports its effectiveness in DOX sensitization to kill the breast cancer cells in vivo. Despite body weight drop observed, DOX/DRI-TAT-SP combination does not cause severe organ alteration. Data provided in the present disclosure support ITGA2 as a new therapeutic target to reverse chemoresistance in breast cancer by disrupting ITGA2/CRT interaction.

The following examples are intended to aid the understanding and enablement of certain embodiments in the present disclosure, which should not be considered as limiting the scope of the present invention.

Examples (A) General DNA Amplification Methods

DNA amplification was conducted by PCR using Phusion polymerase (ThermoFisher Scientific). All sgRNA and cDNA expression plasmids were transformed and stored as glycerol stocks at −80C in E coli cells. All vectors and plasmids used in mammalian cell assays were purified using endotoxin-free DNA plasmid maxiprep kit (Bioteke). Hygromycin B used for either plasmid maintenance or selection were purchased from Invitrogen.

(B) General Mammalian Cell Culture Conditions:

MCF-7 and derived cells were cultured in Minimal Eagles Media (MEM) containing 10% (v/v) fetal bovine serum (FBS), 100U/mL penicillin, 100 μg/mL streptomycin and 0.01 mg/mL human recombinant insulin. CSCs were produced by sorting a CD24$^{low}$/CD44$^{high}$ subpopulation. CSCs or MCF-7-derived MS were cultured in MAMMOCULT™ Human Basal media (STEMCELL TECHNOLOGIES) containing 10% (v/v) MAMMOCULT™ Proliferation Supplement (STEMCELL TECHNOLOGIES), 4 μg/mL Heparin Solution (STEMCELL technologies) and 0.48 μg/mL Hydrocortisone (STEMCELL TECHNOLOGIES). All cell types were incubated, maintained and cultured at 37° C. with 5% $CO_2$.

(C) Generation of ITGA2 KO Clone:

Construction of an expression plasmid for sgRNAs was done as previously reported. Two oligo pairs encoding the 20-nt guide sequences of ITGA2 (Table 2) were annealed and ligated into pSpCas9(BB)-2A-GFP (PX458) plasmid. pSpCas9(BB)-2A-GFP (PX458) was a gift from Feng Zhang (Addgene plasmid #48138). Correct cloning and sequences were confirmed by Sanger sequencing. MCF-7 AC were seeded on 6-well plates and transfected at approximately 70% confluency with 2.5 µg with sgRNAs and 10 ng GFP plasmid expression (generous gift from Dr. Ben Ko), 5 µL Lipofectamine P3000 and 7.5 µL Lipofectamine 3000 (Life Technologies) as per the manufacturer's instructions. Cells were cultured for 48 hours and sorted for GFP fluorescence using FACSAria III Flow Cytometer (Becton Dickenson Bioscience). GFP-positive cells were collected and cultured.

(F) Flow Cytometry Analysis:

Cells were detached by Phosphate buffered saline (PBS) with 2.5 mM EDTA and washed with PBS. For determining CSC population, a total of $1\times10^6$ cells were incubated with APC-CD44 (BD Biosciences) and PE-CD24 (BD Biosciences) in FACS solution (PBS with 1% BSA and 1 mM EDTA) for 30 minutes on ice. APC-IgG2 (BD Biosciences) and PE-IgG2 (BD Biosciences) were used as isotype controls. For determining apoptotic population, a total of $1\times10^6$ cells were first treated with or without 1 µM DOX for 24 hours, in the absence or presence of 1 µM TAT-SP or TAT-SPScr, followed by incubation with FITC-Annexin V (BD Biosciences) and propidium iodide (PI) in binding

TABLE 2

Primers used for generating sgRNA plasmids and mammalian cell genomic DNA amplification:

| Primer | Sequence | SEQ ID NO. |
|---|---|---|
| ITGA2 KO sgRNA-A forward | 5'-CACCGTGTGTTTCTAGGTTACTGGT-3' | 7 |
| ITGA2 KO SgRNA-A reverse | 5'-AAACACCAGTAACCTAGAAACACAC-3' | 8 |
| ITGA2 KO sgRNA-B forward | 5'-CACCGATCAAGCCGAGGCTCATGT-3' | 9 |
| ITGA2 KO SgRNA-B reverse | 5'-AAACACATGAGCCTCGGCTTGATC-3' | 10 |
| ITGA2 sequencing forward | 5'-AGAAAGGCAGCAGGTCAAATC-3' | 11 |
| ITGA2 sequencing reverse | 5'-CCTCAGATTGGGAGGGATGGT-3' | 12 |
| ITGA2 dm forward | 5'-CTCTggTTgCAATTTTATggAAATATgAAAAgATgA-3' | 13 |
| ITGA2 dm reverse | 5'-TTggTCATCTTTTCATATTTCCATAAAATTgCAACC-3' | 14 |

(D) Generation of Overexpression Clones:

pCMV-ITGA2-CH cDNA plasmid was purchased from Sino Biological Inc. for overexpression full-length ITGA2. KLGFFKR (SEQ ID NO: 29) motif was removed by PCR-mediated deletion as previously described with ITGA2 dm primers and pCMV-ITGA2-CH (Sino Biological Inc.) plasmid as template listed in above Table 2. pcDNA 3.1 (+) Tac6 and pcDNA 3.1 (+) TacδScr plasmids were a gift from Chinten James Lim (Addgene plasmid #80019). MCF-7 and A2KO AC were seeded on 6-well plates and transfected at approximately 70% confluency with 2.5 µg cDNA plasmid, 5 µL Lipofectamine P3000 and 7.5 µL Lipofectamine 3000 (Life Technologies) as per the manufacturer's instructions. Cells were selected with 50 µg/mL hygromycin B for 3-5 days and maintained in medium with 10 µg/mL hygromycin B (Invitrogen) for maintenance of cDNA expression.

(E) Chemotherapeutic Drugs and Culture Media:

Doxorubicin (DOX), Paclitaxel (PTX) and Vincristine (VCR), 3-(4,5-Dimethylthiazol-2-yl)-5-[3-(carboxymethoxy)phenyl]-2-(4-sulfo-phenyl)-2H-tetrazolium (MTS) and phenazine methosulfate (PMS) was purchased from Promega. Minimal essential Media (MEM) was purchased from Life Technologies. MAMMOCULT™ Human Basal Media and its supplements were purchased from STEMCELL Technologies. 17β-estradiol pellets (0.72 mg, 60-day release) was purchased from Innovative Research of America (Sarasota, FL).

buffer (10 mM Hepes, pH 7.4, 140 mM NaCl and 2.5 mM $CaCl_2$) for 30 minutes on ice as per the manufacturer's instructions. For determining CRT surface localization, a total of $1\times10^6$ cells, treated with or without 1 µM DOX for 24 hours, were incubated with anti-CRT antibody (1:800, CST) in PBS with 3% BSA for 1 hour on ice. After washing with PBS, cells were further incubated with 2 µg/mL goat anti-rabbit Alexa Fluor 488 (Invitrogen) for 45 minutes on ice. Fluorescence signals were analyzed by BD Accuri C6 flow cytometer (BD Biosciences).

(G) Semi-Quantitative Reverse Transcription-Polymerase Chain Reaction (RT-PCR) and Quantitative Real-Time PCR (qRT-PCR) and $RT^2$ qPCR Primer Assay:

The total RNA was extracted from MCF-7 AC and derived cells using TRIzol reagent (Invitrogen) according to the manufacturer's instructions and reverse-transcribed into cDNA using High Capacity cDNA Reverse Transcription Kits (Applied Biosystems). The primer sequences were designed using Primer Blast and listed as Table 3. qRT-PCR amplification was performed using GOTAQ® qPCR Master Mix (PROMEGA) according to the manufacturer's instructions. The relative mRNA level was normalized to β-actin and the difference in mRNA levels was estimated using the $2^{-\Delta\Delta Ct}$ method. $RT^2$ qPCR Primer Assay was performed using $RT^2$ PROFILER™ PCR array (Qiagen) containing a set of 84 human cancer stem cell-focus genes.

TABLE 3

Primers used for qRT-PCR:

| Primer | | Sequence | SEQ ID NO |
|---|---|---|---|
| ITGA1 | forward | 5'-GGTGCTTATTGGTTCTCCGTTAG-3' | 15 |
| | reverse | 5'-TTCTCCTTTACTTCTGTGACATTGG-3' | 16 |
| ITGA2 | forward | 5'-GGAACGGGACTTTCGCAT-3' | 17 |
| | reverse | 5'-GGTACTTCGGCTTTCTCATCA-3' | 18 |
| ITGA10 | forward | 5'-AGTAAAGGCAGTTGGATTCTCATAGAC-3' | 19 |
| | reverse | 5'-GAGCTGCACTCTGGAGACCAAT-3' | 20 |
| ITGB1 | forward | 5'-AATGAATGCCAAATGGGACACGGG-3' | 21 |
| | reverse | 5'-TTCAGTGTTGTGGGATTTGCACGG-3' | 22 |
| MRP1 | forward | 5'-ATGTCACGTGGAATACCAGC-3' | 23 |
| | reverse | 5'-GAAGACTGAACTCCCTTCCT-3' | 24 |
| β-actin | forward | 5'-CTCTTCCAGCCTTCCTTCCT-3' | 25 |
| | reverse | 5'-AGCACTGTGTTGGCGTACAG-3' | 26 |

(H) Peptide Synthesis:

The peptides were composed of a ubiquitin-like (UBL) domain, SELGFPPAVQRWVIGRCLCVPER (SEQ ID NO: 2), with or without a cell penetrating peptide sequence (TAT), RKKRRQRRR (SEQ ID NO: 1). The DRI-TAT-SP was produced in a reversed sequence using D-amino acids and was protected by acetylation at N-terminus and amidation at C-terminus to make it more resistant to enzymatic degradation.

In certain exemplary embodiments, the following peptides are used to prepare the present composition:
(i) TAT-peptide (SEQ ID NO: 1):
(ii) SHARPIN-derived peptide (SP): SELGFPPAVQRWVIGRCLCVPER (SEQ ID NO: 2);
(iii) TAT-SP peptide: RKKRRQRRRSELGFPPAVQRWVIGRCLCVPER (SEQ ID NO: 4);
(iv) DRI-TAT-SP peptide: Ac-repvclcrgivwrqvappfglesrrrqrrkkr-NH$_2$ (SEQ ID NO: 6), where one-letter amino acid code in upper case denotes L-amino acids; one-letter amino acid code in lower case denotes D-amino acids.

Other peptides such as SPScr (SEQ ID NO: 3) and TAT-SPScr (SEQ ID NO: 5) are used to synthesize comparative compositions in certain assays with the aforementioned exemplary compositions, in particular, to compare with the compositions comprising TAT-SP peptide (SEQ ID NO: 4) and DRI-TAT-SP peptide (SEQ ID NO: 6).

(I) DOX Accumulation Assay:

To assess MRP1 activity, 2×10⁵ MCF-7 AC and derived cells, with or without 24-hour incubation of 1 μM TAT-SP or TAT-SPScr, were treated with 5 μM DOX at 37° C. for 2 hours. After removal of extracellular drugs, cells were divided into two equal halves. One half was lysed with lysis buffer (isopropanol with 0.75 M HCl and 0.2% Triton X-100) at room temperature for 30 minutes; the other half was incubated with 5 μM CMFDA (Invitrogen) in darkness at room temperature for 30 minutes. The fluorescent intensities of drugs and dyes were detected with CLARIOstar (BMG LABTECH) and relative drug concentrations were normalized to CMFDA level.

(J) Immunoprecipitation:

Calreticulin (CRT) from MCF-7-derived cells was immunoprecipitated by anti-CRT (CST) antibody. In brief, MCF-7-derived cells, with or without 24-hour incubation of 1 μM TAT-SP or TAT-SPScr, were collected and subsequently lysed with RIPA buffer on ice for 30 minutes. The lysate was diluted 5-fold with PBS and incubated with anti-CRT antibody overnight at 4° C. with simultaneous mixing on a rotating platform, followed by further incubation of Protein-G PLUS agarose (Santa Cruz Biotechnology) at 4° C. for at least 2 hours.

After incubation, agarose beads were centrifuged and washed by PBS. Immunoprecipitated proteins were collected by treating the beads with 0.2 M glycine and subjected to Western Blotting (WB) analysis.

(K) Protein Preparation and Western Blotting:

Total protein was extracted with RIPA buffer supplied with protease inhibitor (Roche), resolved in 10% SDS-PAGE and transferred onto Immobilon-P PVDF membrane (Millipore). Membranes were blocked with 5% non-fat dry milk in Tris-buffered saline with 0.1% Tween (TBST) for 2 hours, then were incubated overnight with corresponding antibodies at 4° C., followed by incubation with horseradish peroxidase-conjugated goat anti-mouse IgG (Santa Cruz Biotechnology) or goat anti-rabbit IgG (Santa Cruz Biotechnology) as appropriate, for 2 hours at room temperature in TBST. Antibody binding was detected with Pierce ECL Western Blotting Substrate (Thermo Scientific) and images were visualized with Azure C600 imaging system (Azure Biosystems). The antibodies used were anti-ITGA2 (Abcam), anti-CRT (CST), anti-ILR2 (CST), anti-MRP1/ABCC1 (CST), anti-Mdr-1 (Santa Cruz Biotechnology), anti-Akt (pan) (CST), anti-pAkt (S473) (CST), anti-pAkt (T308) (CST), p53 (Santa Cruz Biotechnology) and anti-β-actin (Santa Cruz Biotechnology).

(L) Determination of 50% Inhibitory Concentration ($IC_{50}$) by MTS Assay:

MCF-7 AC and derived cells were seeded onto 96-well plates at a density of 1×10⁴ cells per well and treatments of anticancer drugs or peptides were administered accordingly. Following 72-hour incubation at 37° C. with 5% $CO_2$, cell viability was assessed using CellTiter 96 AQueous Non-Radioactive Cell Proliferation Assay (Promega). The $IC_{50}$ value was estimated from the optical density at 492 nm using GraphPad.

(M) Pharmacokinetic Study of SHARPIN-Derived Peptides:

SHARPIN-derived peptides powder was dissolved in 1×PBS and administered intravenously at 25 mg/kg to overnight-starved Balb/c mice (n=3). At different time points (5, 15, 30, 60, 120, 240, 420 min), blood was collected via cardiac puncture and placed in a heparinized Eppendorf tube followed by centrifuged at 14,000 rpm for 5 min to obtain blood plasma. Plasma was stored at −80° C. until analysis. Plasma concentration data were analyzed by non-compartmental model. Area under plasma concentration-time curve (AUC), distribution half-life ($t_{1/2\alpha}$) and elimination half-life ($t_{1/2\beta}$) were calculated by PK solution2.0 (Summit Research Service, Ashland, USA).

(N) DRI-TAT-SP Accumulation Assay in Tumors:

DRI-TAT-SP 25 mg/kg were administered intravenously to female Balb/c nude mice bearing MCF7 xenograft. At different time points (5, 30, 60, 120 and 240 min), tumors were collected after the sacrifice of the mice. Tumors were weighed and added with 3 volumes of 1×PBS for tissue homogenization. The samples were stored at −80° C. before analysis.

(O) UPLC/QQQ-MS Analysis Protocol:

Agilent 6460 Ultra Performance Liquid Chromatography-Electrospray Ionization Triple Quadrupole mass spectrometer (UPLC-QQQ-MS) was used in sample separation, peptide detection and quantification. Waters Acquity UPLC BEH Protein C4 column (1.7 µm, 2.1×100 mm) was used for separation. SHARPIN-derived peptides were separated and eluted by a gradient of water (0.1% FA, v/v) and acetonitrile (ACN) (0.1% FA, v/v) at a constant flow rate of 0.3 mL/min. During separation, an elution protocol was used as follows. Equilibration: 0 to 1 min, 5% ACN. Elution gradient: 1 to 10 min, ACN from 5 to 99%. Regeneration: 10 to 11 min, 99% ACN, then 11 to 11.5 min, ACN from 99% to 5%. Re-equilibration: 11.5 to 13 min: 5% acetonitrile. A hundred microlitres of plasma/tumor samples were added with 300 µL acetonitrile (1% formic acid (FA)) for protein and peptide precipitation. Supernatants were discarded after centrifugation at 14,000 rpm for 10 minutes. Then the samples were reconstituted in 50% methanol (0.1% FA, v/v), filtered through a 0.22 µm nylon filter, and kept in the autosampler at 4° C. for analysis. Twenty microliters were injected into the MS. The MS was operated in positive electrospray ionization (ESI+) mode with supply of 300° C. gas temperature and sheath gas temperature, 8 L/min drying gas, and 11 L/min sheath gas flow and 3.5 kV capillary voltage. The signals of TAT-SP and DRI-TAT-SP were recorded at m/z 563 to 661 at collision energy (CE) of 15 eV and m/z 569 to 637 at CE of 20 eV, respectively. TAT-SP and DRI-TAT-SP were eluted at 4.05 and 3.86 minutes, respectively.

(P) In Vivo Toxicity Test in Balb/c Mice:

Healthy female Balb/c mice (6-8 weeks old) were randomized into 3 groups and were administered with (1) DOX 1.2 mg/kg i.v., (2) DRI-TAT-SP 25 mg/kg i.v, and (3) DOX 1.2 mg/kg+DRI-TAT-SP 25 mg/kg i.v. once every two days (q2d) for 10 injections via tail vein injection. The body weight of the mice was measured once every 2 days. Any toxicity symptoms including body weight change and behavioral changes will be monitored. Body weight drop more than 15% suggested treatment induced toxicity.

(Q) In Vivo Efficacy Study of DRI-TAT-SP Combined with DOX in Treating MCF7 Breast Cancer Xenograft Model:

Six- to eight-week-old female Balb/c nude mice were maintained under specific pathogen-free conditions prior to in vivo efficacy study. Each animal was implanted with a piece of 170-estradiol pellet 0.72 mg, 60-day release. (Cat No. SE-121, Innovative Research of America, Sarasota, FL). Four days later, the nude mice were inserted at the both flanks with a sesame sized (around 10 mm$^3$) MCF-7 tumor piece originated from a tumor bulk. When the tumor reached approximately 100 mm$^3$ (21-28 days), the mice were randomized and administered intravenously with (1) 1×PBS, (2) DOX 1.2 mg/kg, (3) DRI-TAT-SP 25 mg/kg or (4) DOX 1.2 mg/kg+DRI-TAT-SP 25 mg/kg once every 2 days for a total of 10 injections. Tumor volume was measured using digital caliper once every 4 days. Estimated tumor volume (mm$^3$) was calculated as ½×length (mm)×width (mm)$^2$. The mouse body weights were recorded once every two days. The tumor doubling time (Td) was calculated as t×log 2/log($V_f/V_0$), where t, $V_f$ and $V_0$ stand for interval time, percentage change of tumor volume on final day and percentage change of tumor volume on initial day.

Flow cytometry data were analyzed with BD Accuri C6 software (BD Biosciences). Densitometric analysis was carried out by ImageJ software. Statistical analysis was performed using GraphPad Prism 5 and SPSS. Student t-test was employed to determine significant differences.

Although the invention has been described in terms of certain embodiments, other embodiments apparent to those of ordinary skill in the art are also within the scope of this invention. Accordingly, the scope of the invention is intended to be defined only by the claims which follow.

INDUSTRIAL APPLICABILITY

Figure 9:
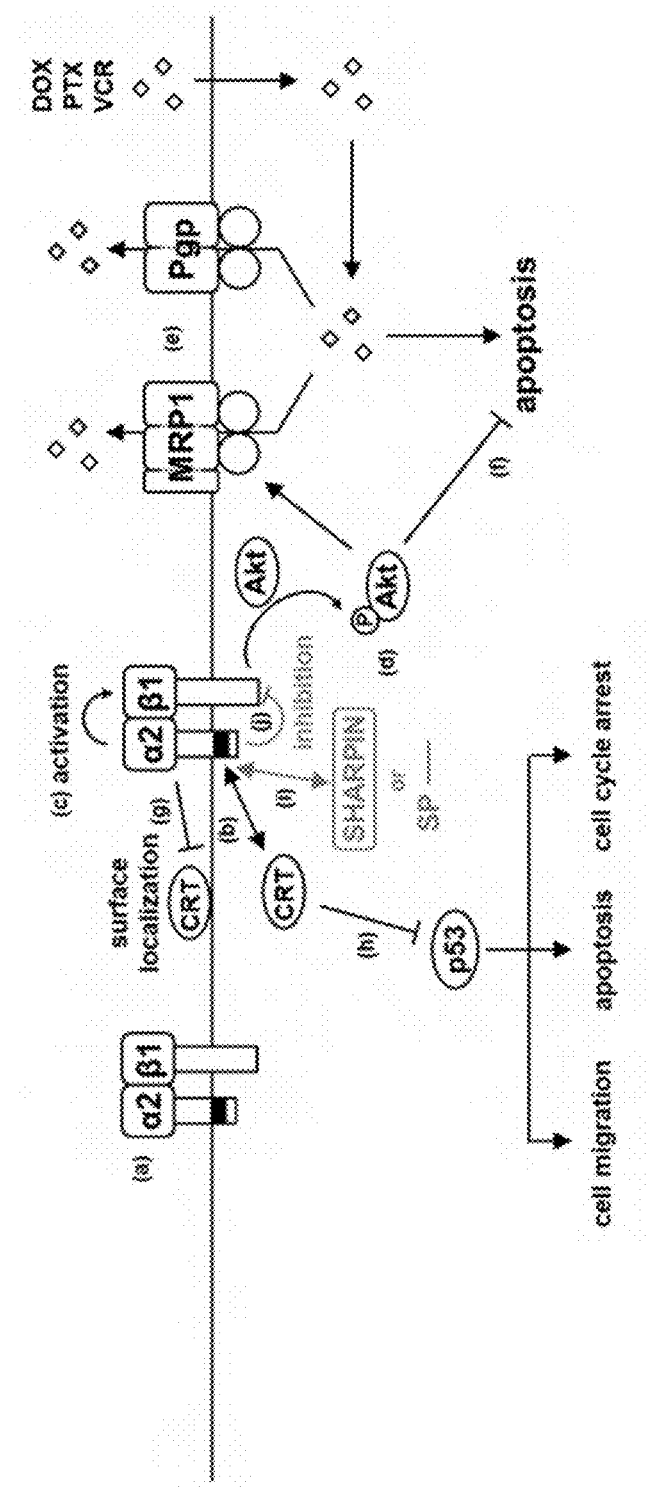
FIG. 9 schematically depicts a proposed mechanism of ITGA2-mediated attachment-independent chemoresistance in CSC, and how it can be inhibited or reversed by the SHARPIN or SHARPIN-derived peptide according to certain embodiments of the present invention.

The proposed disruption of ITGA2/CRT interaction by two SHARPIN-derived peptides, TAT-SP and DRI-TAT-SP, is a new therapeutic target to reverse chemoresistance in breast CSCs (FIG. 9). The proven DRI-TAT-SP efficacies in DOX sensitization in breast cancer cells of in vivo human breast cancer xenograft suggest a novel peptide therapeutic candidate to treat breast cancers. Despite body weight drop observed, the data in the present disclosure supports that DRI-TAT-SP is safe for in vivo application and provides a synergistic effect when being administered in combination with DOX, which in turn lowers the dosage of DOX, ameliorating detrimental side effects from continuous and high dose of DOX administration.

SEQUENCE LISTING

```
Sequence total quantity: 31
SEQ ID NO: 1             moltype = AA  length = 9
FEATURE                  Location/Qualifiers
source                   1..9
                         mol_type = protein
                         organism = synthetic construct
SEQUENCE: 1
RKKRRQRRR                                                                 9

SEQ ID NO: 2             moltype = AA  length = 23
FEATURE                  Location/Qualifiers
source                   1..23
```

```
                              mol_type = protein
                              organism = synthetic construct
SEQUENCE: 2
SELGFPPAVQ RWVIGRCLCV PER                                                 23

SEQ ID NO: 3                  moltype = AA  length = 23
FEATURE                       Location/Qualifiers
source                        1..23
                              mol_type = protein
                              organism = synthetic construct
SEQUENCE: 3
LCRVIVRSPE REAVGPGQPL CFW                                                 23

SEQ ID NO: 4                  moltype = AA  length = 32
FEATURE                       Location/Qualifiers
source                        1..32
                              mol_type = protein
                              organism = synthetic construct
SEQUENCE: 4
RKKRRQRRRS ELGFPPAVQR WVIGRCLCVP ER                                       32

SEQ ID NO: 5                  moltype = AA  length = 32
FEATURE                       Location/Qualifiers
source                        1..32
                              mol_type = protein
                              organism = synthetic construct
SEQUENCE: 5
RKKRRQRRRL CRVIVRSPER EAVGPGQPLC FW                                       32

SEQ ID NO: 6                  moltype = AA  length = 32
FEATURE                       Location/Qualifiers
source                        1..32
                              mol_type = protein
                              organism = synthetic construct
SITE                          1
                              note = D-arginine
SITE                          2
                              note = D-glutamic acid
SITE                          3
                              note = D-proline
SITE                          4
                              note = D-valine
SITE                          5
                              note = D-cysteine
SITE                          6
                              note = D-leucine
SITE                          7
                              note = D-cysteine
SITE                          8
                              note = D-arginine
SITE                          9
                              note = D-glycine
SITE                          10
                              note = D-isoleucine
SITE                          11
                              note = D-valine
SITE                          12
                              note = D-tryptophan
SITE                          13
                              note = D-arginine
SITE                          14
                              note = D-glutamine
SITE                          15
                              note = D-valine
SITE                          16
                              note = D-alanine
SITE                          17
                              note = D-proline
SITE                          18
                              note = D-proline
SITE                          19
                              note = D-phenylalanine
SITE                          20
                              note = D-glycine
SITE                          21
                              note = D-leucine
SITE                          22
                              note = D-glutamic acid
SITE                          23
```

```
                            note = D-serine
SITE                        24
                            note = D-arginine
SITE                        25
                            note = D-arginine
SITE                        26
                            note = D-arginine
SITE                        27
                            note = D-glutamine
SITE                        28
                            note = D-arginine
SITE                        29
                            note = D-arginine
SITE                        30
                            note = D-lysine
SITE                        31
                            note = D-lysine
SITE                        32
                            note = D-arginine
SEQUENCE: 6
REPVCLCRGI VWRQVAPPFG LESRRRQRRK KR                              32

SEQ ID NO: 7                moltype = DNA  length = 25
FEATURE                     Location/Qualifiers
source                      1..25
                            mol_type = other DNA
                            organism = synthetic construct
misc_feature                1..25
                            note = ITGA2 KO sgRNA-A forward primer
SEQUENCE: 7
caccgtgtgt ttctaggtta ctggt                                     25

SEQ ID NO: 8                moltype = DNA  length = 25
FEATURE                     Location/Qualifiers
source                      1..25
                            mol_type = other DNA
                            organism = synthetic construct
misc_feature                1..25
                            note = ITGA2 KO sgRNA-A reverse primer
SEQUENCE: 8
aaacaccagt aacctagaaa cacac                                     25

SEQ ID NO: 9                moltype = DNA  length = 24
FEATURE                     Location/Qualifiers
source                      1..24
                            mol_type = other DNA
                            organism = synthetic construct
misc_feature                1..24
                            note = ITGA2 KO sgRNA-B forward primer
SEQUENCE: 9
caccgatcaa gccgaggctc atgt                                      24

SEQ ID NO: 10               moltype = DNA  length = 24
FEATURE                     Location/Qualifiers
source                      1..24
                            mol_type = other DNA
                            organism = synthetic construct
misc_feature                1..24
                            note = ITGA2 KO sgRNA-B reverse primer
SEQUENCE: 10
aaacacatga gcctcggctt gatc                                      24

SEQ ID NO: 11               moltype = DNA  length = 21
FEATURE                     Location/Qualifiers
source                      1..21
                            mol_type = other DNA
                            organism = synthetic construct
misc_feature                1..21
                            note = ITGA2 sequencing forward primer
SEQUENCE: 11
agaaaggcag caggtcaaat c                                         21

SEQ ID NO: 12               moltype = DNA  length = 21
FEATURE                     Location/Qualifiers
source                      1..21
                            mol_type = other DNA
                            organism = synthetic construct
misc_feature                1..21
                            note = ITGA2 sequencing reverse primer
```

```
SEQUENCE: 12
cctcagattg ggagggatgg t                                                 21

SEQ ID NO: 13           moltype = DNA  length = 36
FEATURE                 Location/Qualifiers
source                  1..36
                        mol_type = other DNA
                        organism = synthetic construct
misc_feature            1..36
                        note = ITGA2 dm forward primer
SEQUENCE: 13
ctctggttgc aattttatgg aaatatgaaa agatga                                 36

SEQ ID NO: 14           moltype = DNA  length = 36
FEATURE                 Location/Qualifiers
source                  1..36
                        mol_type = other DNA
                        organism = synthetic construct
misc_feature            1..36
                        note = ITGA2 dm reverse primer
SEQUENCE: 14
ttggtcatct tttcatattt ccataaaatt gcaacc                                 36

SEQ ID NO: 15           moltype = DNA  length = 23
FEATURE                 Location/Qualifiers
source                  1..23
                        mol_type = other DNA
                        organism = synthetic construct
misc_feature            1..23
                        note = ITGA1 qRT-PCR forward primer
SEQUENCE: 15
ggtgcttatt ggttctccgt tag                                               23

SEQ ID NO: 16           moltype = DNA  length = 25
FEATURE                 Location/Qualifiers
source                  1..25
                        mol_type = other DNA
                        organism = synthetic construct
misc_feature            1..25
                        note = ITGA1 qRT-PCR reverse primer
SEQUENCE: 16
ttctccttta cttctgtgac attgg                                             25

SEQ ID NO: 17           moltype = DNA  length = 18
FEATURE                 Location/Qualifiers
source                  1..18
                        mol_type = other DNA
                        organism = synthetic construct
misc_feature            1..18
                        note = ITGA2 qRT-PCR forward primer
SEQUENCE: 17
ggaacgggac tttcgcat                                                     18

SEQ ID NO: 18           moltype = DNA  length = 21
FEATURE                 Location/Qualifiers
source                  1..21
                        mol_type = other DNA
                        organism = synthetic construct
misc_feature            1..21
                        note = ITGA2 qRT-PCR reverse primer
SEQUENCE: 18
ggtacttcgg ctttctcatc a                                                 21

SEQ ID NO: 19           moltype = DNA  length = 27
FEATURE                 Location/Qualifiers
source                  1..27
                        mol_type = other DNA
                        organism = synthetic construct
misc_feature            1..27
                        note = ITGA10 qRT-PCR forward primer
SEQUENCE: 19
agtaaaggca gttggattct catagac                                           27

SEQ ID NO: 20           moltype = DNA  length = 22
FEATURE                 Location/Qualifiers
source                  1..22
                        mol_type = other DNA
                        organism = synthetic construct
misc_feature            1..22
```

```
                        note = ITGA10 qRT-PCR reverse primer
SEQUENCE: 20
gagctgcact ctggagacca at                                            22

SEQ ID NO: 21           moltype = DNA   length = 24
FEATURE                 Location/Qualifiers
source                  1..24
                        mol_type = other DNA
                        organism = synthetic construct
misc_feature            1..24
                        note = ITGB1 qRT-PCR forward primer
SEQUENCE: 21
aatgaatgcc aaatgggaca cggg                                          24

SEQ ID NO: 22           moltype = DNA   length = 24
FEATURE                 Location/Qualifiers
source                  1..24
                        mol_type = other DNA
                        organism = synthetic construct
misc_feature            1..24
                        note = ITGB1 qRT-PCR reverse primer
SEQUENCE: 22
ttcagtgttg tgggatttgc acgg                                          24

SEQ ID NO: 23           moltype = DNA   length = 20
FEATURE                 Location/Qualifiers
source                  1..20
                        mol_type = other DNA
                        organism = synthetic construct
misc_feature            1..20
                        note = MRP1 qRT-PCR forward primer
SEQUENCE: 23
atgtcacgtg gaataccagc                                               20

SEQ ID NO: 24           moltype = DNA   length = 20
FEATURE                 Location/Qualifiers
source                  1..20
                        mol_type = other DNA
                        organism = synthetic construct
misc_feature            1..20
                        note = MRP1 qRT-PCR reverse primer
SEQUENCE: 24
gaagactgaa ctcccttcct                                               20

SEQ ID NO: 25           moltype = DNA   length = 20
FEATURE                 Location/Qualifiers
source                  1..20
                        mol_type = other DNA
                        organism = synthetic construct
misc_feature            1..20
                        note = Beta-actin qRT-PCR forward primer
SEQUENCE: 25
ctcttccagc cttccttcct                                               20

SEQ ID NO: 26           moltype = DNA   length = 20
FEATURE                 Location/Qualifiers
source                  1..20
                        mol_type = other DNA
                        organism = synthetic construct
misc_feature            1..20
                        note = Beta-actin qRT-PCR reverse primer
SEQUENCE: 26
agcactgtgt tggcgtacag                                               20

SEQ ID NO: 27           moltype = AA    length = 32
FEATURE                 Location/Qualifiers
source                  1..32
                        mol_type = protein
                        organism = synthetic construct
SEQUENCE: 27
KLGFFKRKYE KMTKNPDEID ETTELSSGGG GS                                 32

SEQ ID NO: 28           moltype = AA    length = 25
FEATURE                 Location/Qualifiers
source                  1..25
                        mol_type = protein
                        organism = synthetic construct
SEQUENCE: 28
KYEKMTKNPD EIDETTELSS GGGGS                                         25
```

```
SEQ ID NO: 29          moltype = AA  length = 7
FEATURE                Location/Qualifiers
source                 1..7
                       mol_type = protein
                       organism = synthetic construct
SEQUENCE: 29
KLGFFKR                                                                7

SEQ ID NO: 30          moltype = AA  length = 7
FEATURE                Location/Qualifiers
source                 1..7
                       mol_type = protein
                       organism = synthetic construct
SEQUENCE: 30
KLRFGFK                                                                7

SEQ ID NO: 31          moltype = AA  length = 7
FEATURE                Location/Qualifiers
source                 1..7
                       mol_type = protein
                       organism = synthetic construct
SEQUENCE: 31
KXGFFKR                                                                7
```

What is claimed is:

1. A composition comprising a peptide, the peptide comprising a TAT peptide represented by SEQ ID NO:1 and a Shank-associated RH domain-interacting protein (SHARPIN) represented by SEQ ID NO:2; or a retro-inverso peptide thereof, wherein the TAT peptide is directly bound to the SHARPIN peptide (SP).

2. The composition of claim 1, wherein the TAT peptide and SHARPIN-derived peptide are synthesized together into a D-retro-inverso (DRI) form.

3. The composition of claim 2, wherein the SHARPIN-derived peptide is synthesized based on D-amino acids for preventing from protease digestion when the composition is administered to a subject in need thereof.

4. The composition of claim 3, wherein the DRI-TAT-SP peptide is modified at the N- and C-termini thereof.

5. The composition of claim 4, wherein the N-terminus of the DRI-TAT-SP peptide is acetylated while the C-terminus thereof is amidated.

6. The composition of claim 4, wherein the DRI-TAT-SP peptide comprises SEQ ID NO: 6.

7. The composition of claim 1, wherein the peptide comprises SEQ ID NO: 4.

8. A method for treating multi-drug resistant breast cancer comprising administering to a subject in need thereof a combination of an effective amount of the composition of claim 1 and an effective amount of one or more chemotherapeutic agents.

9. The method of claim 8, wherein the one or more chemotherapeutic agents comprise an anthracycline or DNA topoisomerase II inhibitor.

10. The method of claim 8, wherein the one or more chemotherapeutic agents comprise doxorubicin (DOX), paclitaxel (PTX) or vincristine (VCR).

11. The method of claim 8, wherein the composition is administered to the subject via one or more routes selected from the group consisting of intravenous and intraperitoneal injections.

12. The method of claim 8, wherein the composition comprises a peptide represented by SEQ ID NO: 4.

13. The method of claim 12, wherein the peptide is synthesized into a D-retro-inverso (DRI) form and represented by SEQ ID NO: 6.

14. The method of claim 8, wherein the subject is human and the multi-drug resistant breast cancer is human breast cancer.

* * * * *